(12) United States Patent
Drake et al.

(10) Patent No.: US 11,724,037 B2
(45) Date of Patent: Aug. 15, 2023

(54) ELASTOMER ARTICLES HAVING EMBEDDED ELECTRONICS AND METHODS OF MANUFACTURING THE SAME

(71) Applicant: West Pharmaceutical Services, Inc., Exton, PA (US)

(72) Inventors: Kerry Drake, Red Hill, PA (US); Patrick Dowling, Dublin (IE); Michael Sullivan, Birdsboro, PA (US); Jason Krizan, Elkton, MD (US)

(73) Assignee: West Pharmaceutical Services, Inc., Exton, PA (US)

( * ) Notice: Subject to any disclaimer, the term of this patent is extended or adjusted under 35 U.S.C. 154(b) by 212 days.

(21) Appl. No.: 16/618,990

(22) PCT Filed: Jun. 6, 2018

(86) PCT No.: PCT/US2018/036194
§ 371 (c)(1),
(2) Date: Dec. 3, 2019

(87) PCT Pub. No.: WO2018/226782
PCT Pub. Date: Dec. 13, 2018

(65) Prior Publication Data
US 2021/0121635 A1    Apr. 29, 2021

Related U.S. Application Data

(60) Provisional application No. 62/515,775, filed on Jun. 6, 2017.

(51) Int. Cl.
*A61M 5/315*    (2006.01)
*G16H 20/17*    (2018.01)
*A61M 5/24*    (2006.01)

(52) U.S. Cl.
CPC .......... *A61M 5/31511* (2013.01); *A61M 5/24* (2013.01); *A61M 5/31515* (2013.01);
(Continued)

(58) Field of Classification Search
CPC .................................................. A61M 2205/60
See application file for complete search history.

(56) References Cited

U.S. PATENT DOCUMENTS 2,451,913 A    10/1948  Brice
3,350,252 A    10/1967  Herman
(Continued)

FOREIGN PATENT DOCUMENTS

CN    103702701 A    4/2014
CN    106018230 A    10/2016
(Continued)

OTHER PUBLICATIONS

Int'l Search Report and Writtien Opinion dated Sep. 12, 2018 in Int'l Application No. PCT/US2018/036194.
(Continued)

*Primary Examiner* — Jenna Zhang
(74) *Attorney, Agent, or Firm* — Blank Rome LLP

(57) ABSTRACT

An assembly for a container to be filled with a pharmaceutical drug is provided. The assembly includes a first component and a second component. The first component has at least one electronic device fully embedded therein, a first end provided with a first engagement feature and an opposing second end. The second component has a second engagement feature configured to engage the first engagement feature of the first component.

24 Claims, 28 Drawing Sheets

(52) U.S. Cl.
CPC ........ *A61M 5/31568* (2013.01); *G16H 20/17* (2018.01); *A61M 2205/3553* (2013.01); *A61M 2205/50* (2013.01); *A61M 2205/60* (2013.01); *A61M 2205/6009* (2013.01); *A61M 2205/8206* (2013.01)

(56) References Cited

U.S. PATENT DOCUMENTS

| | | | |
|---|---|---|---|
| 4,248,818 | A | 2/1981 | Elizabeth |
| 4,997,423 | A * | 3/1991 | Okuda ................ A61M 5/2429 604/218 |
| 5,808,203 | A | 9/1998 | Nolan, Jr. et al. |
| 5,955,021 | A | 9/1999 | Tiffany, III |
| 6,105,248 | A | 8/2000 | Tani |
| 6,693,441 | B2 | 2/2004 | Lane et al. |
| 6,743,202 | B2 | 6/2004 | Hirschman et al. |
| 6,837,021 | B2 | 1/2005 | Sudo |
| 7,195,609 | B2 | 3/2007 | Huegli |
| 8,282,013 | B2 | 10/2012 | Stewart et al. |
| 8,773,660 | B2 | 7/2014 | Pommereau et al. |
| 9,413,061 | B2 | 8/2016 | Battocchio |
| 9,855,389 | B2 | 1/2018 | Pommereau et al. |
| 10,076,609 | B2 | 9/2018 | Ashby et al. |
| 10,082,830 | B2 | 9/2018 | Lettow |
| 10,096,896 | B2 | 10/2018 | Mueller et al. |
| 10,704,944 | B2 | 7/2020 | Searle et al. |
| 2001/0034506 | A1 * | 10/2001 | Hirschman ....... A61M 5/14546 604/207 |
| 2003/0233075 | A1 * | 12/2003 | Huegli .................. A61M 5/486 604/222 |
| 2004/0083666 | A1 | 5/2004 | Sudo |
| 2007/0069418 | A1 | 3/2007 | Liao et al. |
| 2009/0005729 | A1 * | 1/2009 | Hendrixson ....... G05B 19/0428 604/246 |
| 2011/0009925 | A1 | 1/2011 | Leigh et al. |
| 2011/0240747 | A1 | 10/2011 | Stewart et al. |
| 2012/0195182 | A1 * | 8/2012 | Pommereau ........ A61M 5/2422 369/127 |
| 2014/0062036 | A1 * | 3/2014 | Maeda .............. A61M 5/31513 277/615 |
| 2014/0333492 | A1 | 11/2014 | Battocchio |
| 2015/0217059 | A1 | 8/2015 | Ashby et al. |
| 2016/0074587 | A1 | 3/2016 | Searle et al. |
| 2016/0151558 | A1 | 6/2016 | Tobescu |
| 2016/0259913 | A1 | 9/2016 | Yu et al. |
| 2016/0287800 | A1 * | 10/2016 | Nakano ................... B29C 59/16 |
| 2017/0005406 | A1 | 1/2017 | Mueller et al. |
| 2017/0082456 | A1 | 3/2017 | Sakate et al. |
| 2017/0312430 | A1 * | 11/2017 | Schleicher ......... A61M 5/31511 |
| 2018/0193567 | A1 * | 7/2018 | Schleicher .......... A61M 5/1684 |
| 2021/0308382 | A1 | 10/2021 | Krizan |

FOREIGN PATENT DOCUMENTS

| | | |
|---|---|---|
| CN | 106062448 A | 10/2016 |
| EP | 1908487 A1 | 4/2008 |
| JP | S5566365 A | 5/1980 |
| JP | 2002518108 A | 6/2002 |
| JP | 2013505433 A | 2/2013 |
| JP | 2015179829 A | 10/2015 |
| WO | 9965548 A1 | 12/1999 |
| WO | 2004/086492 A1 | 10/2004 |
| WO | 2011032956 A2 | 3/2011 |
| WO | 2015103563 A1 | 7/2015 |
| WO | 2015139962 A1 | 9/2015 |
| WO | 2018/226780 A1 | 12/2018 |

OTHER PUBLICATIONS

Int'l Preliminary Report on Patentability dated Oct. 15, 2019 in Int'l Application No. PCT/US2018/036194.

Office Action dated Mar. 2, 2021 in Japanese Application No. 2019-566867.

Office Action dated Apr. 1, 2021 in Chinese Application No. 20188037372.8.

Office Action dated May 8, 2021 in Chinese Application No. 201880037373.2.

Office Action dated on Jun. 3, 2021 in Indian Application No. 201927051080.

Office Action dated Jun. 15, 2021 in Japanese Application No. 2019-566865.

Third Party Submission dated Feb. 5, 2021 in European Application No. 18734390.0.

Fassler, Andrew, and Carmel Majidi "3D structures of liquid-phase Gain alloy embedded in PDMS with freeze casting." Lab on a Chip 13.22 (Sep. 5, 2013): 4442-4450. (Year: 2013).

Int'l Search Report and Written Opinion dated Oct. 15, 2018 in Int'l Application No. PCT/US2018/036191.

* cited by examiner

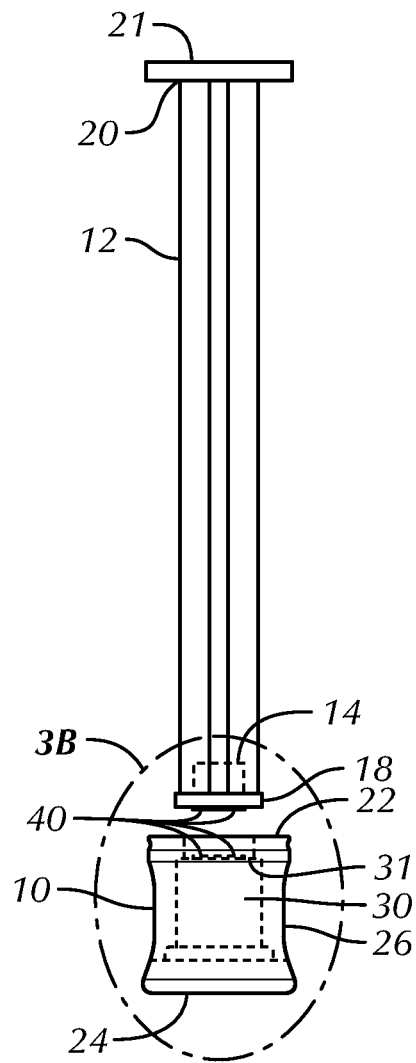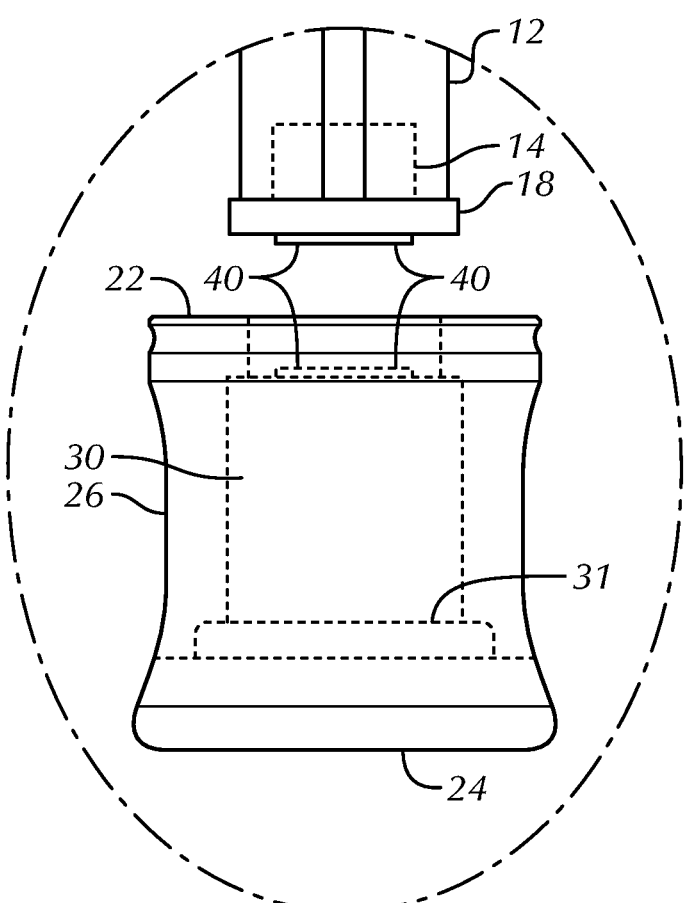
FIG. 3A
FIG. 3B

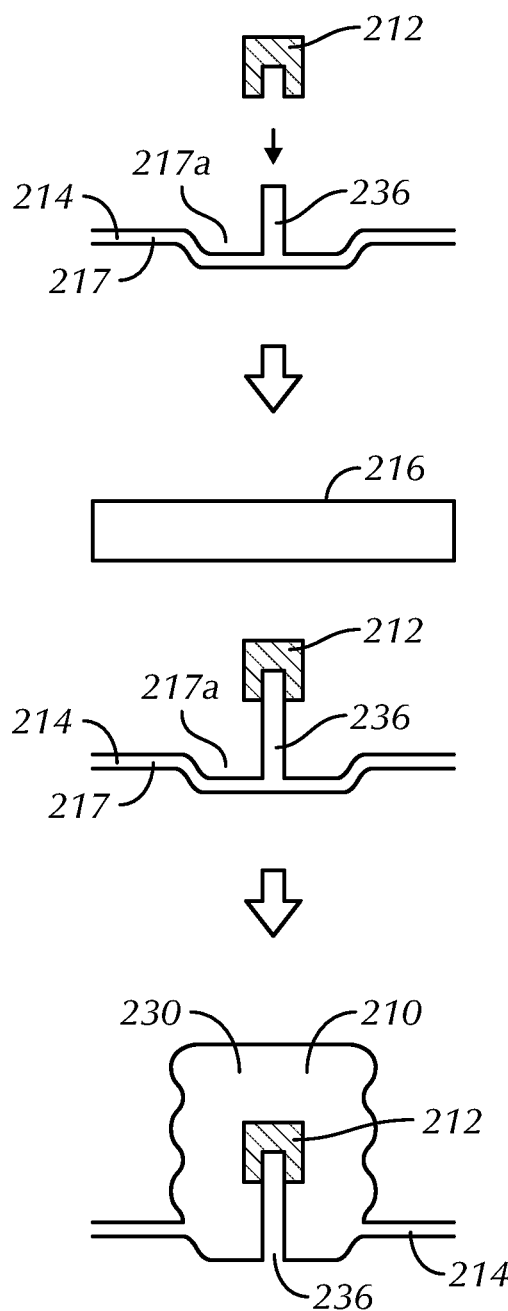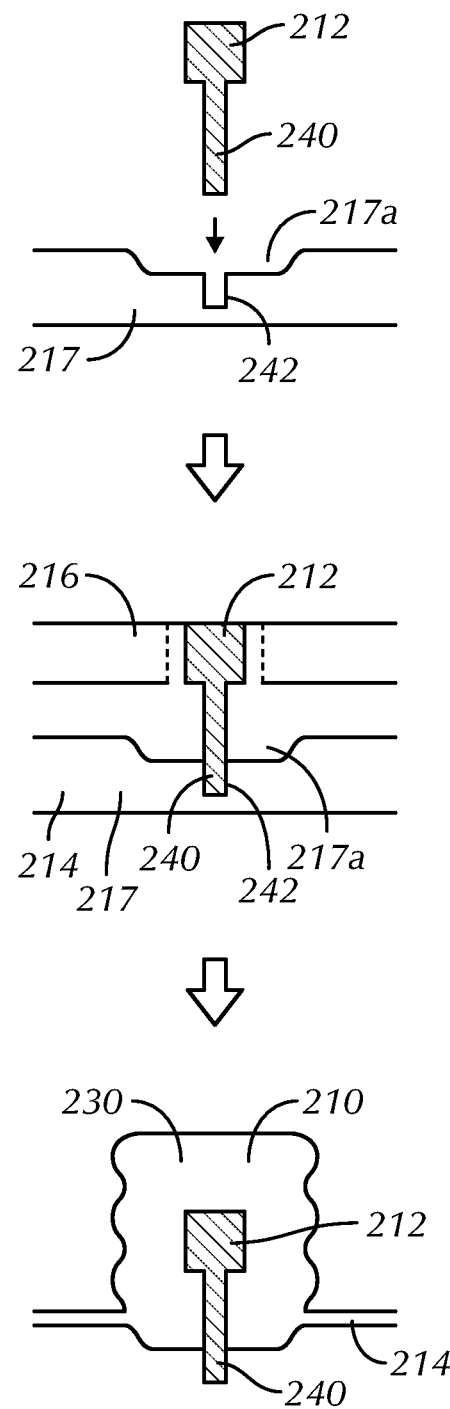
*FIG. 11C*  *FIG. 11D*

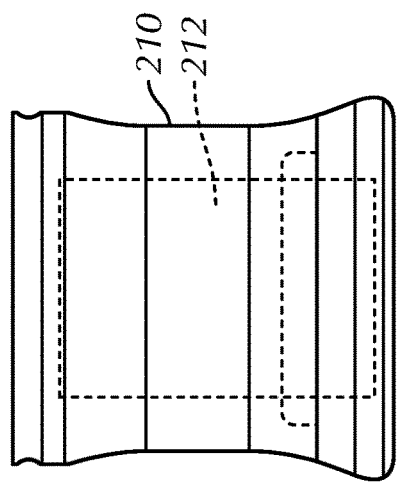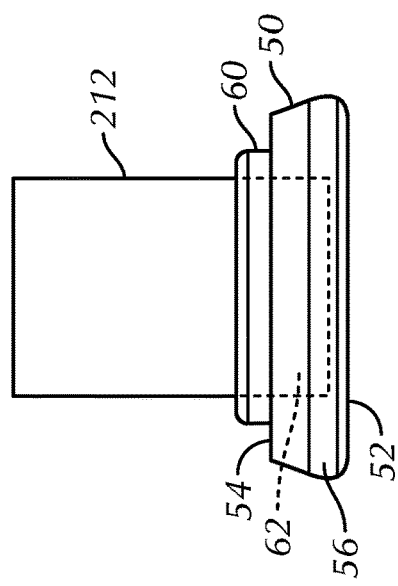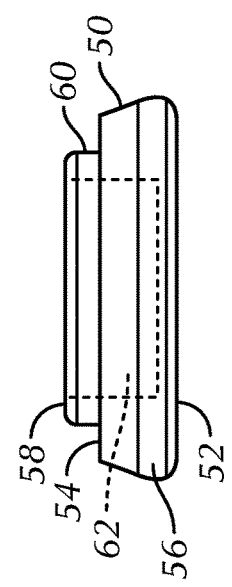

ELASTOMER ARTICLES HAVING EMBEDDED ELECTRONICS AND METHODS OF MANUFACTURING THE SAME

CROSS-REFERENCE TO RELATED APPLICATIONS

This application is a section 371 of International Application No. PCT/US2018/036194, filed Jun. 6, 2018, which was published on Dec. 13, 2018 under International Publication No. WO 2018/226782 A1, and which claims priority from U.S. Provisional Patent Application No. 62/515,775, filed Jun. 6, 2017, the disclosure of which is herein incorporated by reference.

BACKGROUND OF THE INVENTION

The present invention relates generally to elastomer articles having electronics embedded therein and, more particularly, to molded elastomer articles having one or more embedded electronic devices.

It is desirable to enable drug delivery devices to communicate an operational status of the device (e.g., pre-use and/or dosage complete conditions), identification information, other conditions (e.g., ambient temperature), and the like to enable monitoring of a patient or for like purposes. Such devices are known as "smart" devices.

Conventional "smart" devices tend to comprise multiple parts of at least two different materials. For example, one known syringe plunger device is formed of two pieces, one piece being formed of an elastomeric material and another piece being formed of a different plastic or elastomeric material, with an electronic circuit at the interface between the two plunger pieces. Other conventional "smart" devices include conventional electronic components, including sensors, in plungers, where the electronic components are encapsulated in a first component formed of first elastomeric material formable at lower temperatures that the electronic components can withstand, and then the formed first component is encapsulated in a second elastomeric material, to form the plunger. That is, the prior art smart plungers are three-piece plungers.

The present invention provides new and improved elastomer articles with embedded electronics for containers for pharmaceutical containment. The present invention also allows for greater control in how the electronics are positioned and can better work around the requirements of the electronics.

BRIEF SUMMARY OF THE INVENTION

The present invention relates an assembly of components, such as a piston, plunger, closure or stopper, of a medical device or container, such as a cartridge, syringe or vial, comprising a molded elastomeric body and at least one electronic device embedded within and fully encapsulated by the elastomeric material of the component.

One preferred embodiment of the present invention is directed an assembly for a container to be filled with a pharmaceutical drug. The assembly includes a first component and a second component. The first component has at least one electronic device embedded therein, a first end provided with a first engagement feature and an opposing second end. The second component has a second engagement feature configured to engage the first engagement feature of the first component.

Another preferred embodiment of the present invention relates to an assembly for a container to be filled with a pharmaceutical drug. The assembly includes a first component having a first end and an opposing second end, the first end having at least one electronic device embedded therein, at least one exposed electrical contact connected to the electronic device, and a first engagement feature; and a second component having a second engagement feature configured to engage the first engagement feature of the first component and at least one exposed electrical contact configured to engage with the at least one exposed electrical contact of the first component. In an assembled position, the at least one exposed electrical contact of the first component is in electrical communication with the at least one exposed electrical contact of the second component.

Another preferred embodiment of the present invention relates to an assembly for a container to be filled with a pharmaceutical drug. The assembly comprises a first component having at least one magnetic material embedded therein, the first component having a first end provided with a first engagement feature and an opposing second end; and a second component having a second engagement feature configured to engage the first engagement feature of the first component.

Another preferred embodiment of the present invention relates to a system for adjusting the dose of an injectable medicine. The system comprises an assembly for a container to be filled with a pharmaceutical drug, a transducer, a wireless communication unit and a controller. The assembly comprises a first component having at least one electronic device embedded therein, the first component having a first end provided with a first engagement feature and an opposing second end; and a second component having a second engagement feature configured to engage the first engagement feature of the first component. The controller is configured to receive data associated with an administered dose of the injectable medicine and assess whether the administered dose meets one or more prescribed parameters.

Another preferred embodiment of the present invention relates to a method for adjusting the dose of an injectable medicine. The method comprises obtaining a system comprising an assembly for a container to be filled with a pharmaceutical drug, a transducer, a wireless communication unit, and a controller. The assembly comprises a first component having at least one electronic device embedded therein, the first component having a first end provided with a first engagement feature and an opposing second end; and a second component having a second engagement feature configured to engage the first engagement feature of the first component. The method further includes receiving, by the controller, data associated with an administered dose of the injectable medicine; and assessing, by the controller, whether the administered dose meets one or more prescribed parameters.

Advantageous refinements of the invention are specified in the dependent claims. These refinements can be implemented alone or in any combination with each other.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 3A-3B are side elevational views of a piston and piston rod assembly including an embedded electronic device according to another preferred embodiment of the present invention;

FIGS. 11A-11E illustrate methods of manufacturing a medical component in a one-step molding process according to other preferred embodiments of the present invention;

FIGS. 26A-27C illustrate medical components having a notch of various configurations according to another preferred embodiment of the present invention;

FIGS. 27A-27C illustrate a method of manufacturing a medical component in a two-step molding process according to another preferred embodiment of the present invention;

DETAILED DESCRIPTION OF THE INVENTION

Figure 1A:
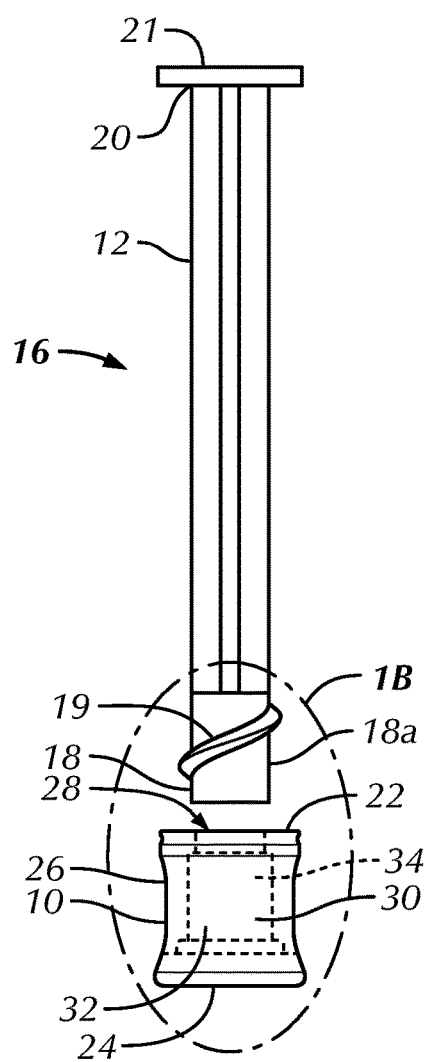
FIGS. 1A-1B are side elevational views of a piston and piston rod assembly including an embedded electronic device according to a preferred embodiment of the present invention.

Certain terminology is used in the following description for convenience only and is not limiting. The words "proximal," "distal," "upward," "downward," "bottom" and "top" designate directions in the drawings to which reference is made. The words "inwardly" and "outwardly" refer to directions toward and away from, respectively, a geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1A-5 show preferred embodiments of components of a medical device provided with an electronic device embedded therein. More particularly, FIGS. 1A-5 show various embodiments of an assembly 16 comprising a first component 10, for example a piston 10, and a second component 12, for example a piston rod 12. It will be understood by those skilled in the art that the term piston may be used interchangeably herein with the term plunger, stopper, closure and the like.

It will also be understood that the assembly 16 may be utilized in any known medical device, and more particularly in any container having a cavity or a chamber capable of being filled with a substance. For example, the container may be, without limitation, a syringe, a cartridge, a vial and the like. More particularly, the medical device may be a cartridge, a syringe with needles, a needleless syringe, an inhaler, a solid dosage dispenser, a pen-type injector, an autoinjector, a wearable injector, a vial and the like.

It will be understood that the invention described herein may be applicable to any two-part assembly for containers for pharmaceutical containment or contact, such as a cartridge piston (plunger, stopper or closure), a syringe piston (plunger, stopper or closure), a vial piston (plunger, stopper or closure), a seal, a gasket, a component of a pre-filled cartridge, a component of a pre-filled syringe, a sleeve or container stopper, a flashback bulb, a cap, a liner, a washer, or any other component/device which may be in contact with pharmaceutically pure materials or medicament.

In a preferred embodiment, the pharmaceutical medicament with which the assembly 16 may be used is insulin (or any derivative, formulation or analog thereof). For example, as used herein, the term "insulin" shall mean insulin, insulin analogs, insulin derivatives or mixtures thereof, including human insulin or a human insulin analogs or derivatives. Examples of insulin analogs include, but are not limited to, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives include, but are not limited to, B29-N-myristoyl-des(B30) human insulin; B29-N-palmitoyl-des (B30) human insulin; B29-N-myristoyl human insulin; B29-Npalmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N (N-palmitoyl-Y-glutamyl)-des(B30) human insulin; B29-N (N-lithocholyl-Y-glutamyl)-des(B30) human insulin; B29-N-(w-carboxyheptadecanoyl)-des(B30) human insulin and B29-N-(w-carboxyheptadecanoyl) human insulin.

For some diabetics, in particular, dosages frequently change and need to be calculated based on meals, time, and formulation. A patient may thus have to juggle multiple daily injections of insulin, such as quick-release (meal-time) insulin or long-acting (once-daily) insulin. The smart device of the present invention facilitates calculating dosages, tracking dosages (i.e., which drug, amount and time) and preventing accidental over/under doses. Improved integration of insulin treatments can therefore clearly help minimize the impact of diabetes on the patient and assist care-givers with feedback to better manage treatment. Such dosage calculation/tracking features are also useful for many other types of pharmaceutical medicaments and many other types of illnesses or conditions, such as, but not limited to multiple sclerosis and arthritis. The smart device of the present invention is especially pertinent for biologic drugs/enzymes for, for example, monitoring of transport conditions (e.g., ensuring that the cold chain and/or dark storage was maintained for efficacy of the drug), because these types of drugs are significantly less stable than many other drugs, and thus would benefit from "smart" technology to ensure consistency and patient safety. However, it will be understood that the assembly 16 may be used with any known or yet to be developed pharmaceutical medicament.

The piston 10 is preferably made of a polymeric material, and more preferably of an elastomeric material. In a preferred embodiment, the elastomeric material is either a thermoset elastomer or a thermoplastic elastomer (TPE). For example, the elastomeric material used for the elastomeric closure can be, for example, a synthetic or natural rubber, such as butyl rubber, isoprene rubber, butadiene rubber, halogenated butyl rubber (e.g., bromobutyl rubber), ethylene propylene terpolymer, silicone rubber, combinations thereof and the like. Preferably, the elastomeric material is a butyl or halobutyl elastomer. The piston 10 may be formed as any known conventional syringe piston.

Figure 1B:
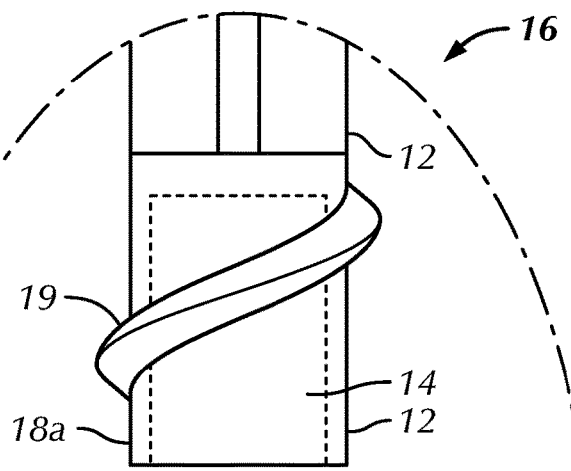

Preferably, the piston 10 has a generally cylindrical body including a first end 22 formed as an open end, an opposing second end 24 formed as a closed base wall, and a tubular sidewall 26 extending therebetween. The closed base wall 24, the open end 22, and the tubular sidewall 26 define an interior 28 of the piston 10. The interior 28 preferably includes an inner cylindrical member 30. The inner cylindrical member 30 is configured to engage or mate with the piston rod 12. In one embodiment, as shown in FIGS. 1A-1B, the inner cylindrical member 30 is formed as a tubular sidewall 32 surrounding a recess 34.

The piston rod 12 has a first end 18 and an opposing second end 20. The first end 18 defines a distal tip of the piston rod 12 which is configured to engage or mate with the piston 10, and more particularly the inner cylindrical member 30 of the piston 10. The second end 20 of the piston rod 12 includes or is formed as a peripheral flange 21. The piston rod 12 may be made of the same polymeric material as that of the piston 10, or alternatively may be formed of a different polymeric material. Alternatively, only a portion of the piston rod 12 (e.g., the first end 18) may be formed of the same polymeric material as that of the piston 10.

The first end 18 of the piston rod 12 includes an electronic device 14 either embedded therein or attached thereto. The electronic device 14 may be embedded in or attached to the first end 18 of the piston rod 12 by any known method. Some exemplary methods for forming an elastomeric molded component with the electronic device 14 embedded therein and fully encapsulated by the elastomeric material are disclosed herein.

The electronic device 14 may comprise any known electronic circuitry, electronic coding, microprocessor, sensor and the like. For example, the electronic device 14 may comprise one or more of an integrated circuit (or electronic chip or microchip), a radio-frequency identification (RFID) chip/coil/antenna and supporting components, a near-field communication (NFC) chip, an EEPROM chip, a solid state memory, a muscle wire, a piezoelectric sensor or actuator, a thermal sensor (e.g., a thermistor or a PTC thermistor), a pressure sensor, a level sensor, a dosage sensor, a mechanical sensor, an electromagnetic sensor, an optical sensor, a pneumatic sensor, a hydraulic sensor, a photosensitive sensor, a flow sensor, a power supply (e.g., a RF induction coil, a miniature coin battery, a super capacitor), a haptic feedback device (e.g., an LED or piezoelectric device) and the like. The electronic device 14 may be further equipped with a transducer and a communication unit, preferably with a wireless communication unit (e.g., bluetooth or bluetooth low energy) by way of which the content of stored data can be retrieved on demand. For example, the electronic device 14 may be comprise a RFID element enabling communication with a corresponding reading device in a wireless way. This way, counterfeited medical components can be easily detected.

Referring to FIGS. 1A-1B, in one embodiment, the electronic device 14 is embedded within an interior of the body of the first end 18 of the piston rod 12 and the exterior surface 18*a* of the first end 18 includes exterior threads 19. In turn, the interior surface of the tubular sidewall 32 of the inner cylindrical member 30 of the piston 10 includes interior threads (not shown) configured to mate with the exterior threads 19. As such, the first end 18 of the piston rod 12 which includes an electronic device 14 embedded therein may be threadingly received within the recess 34 of the piston 10, thereby creating a piston/piston rod assembly 16 provided with an embedded electronic device 14.

Figure 2A:
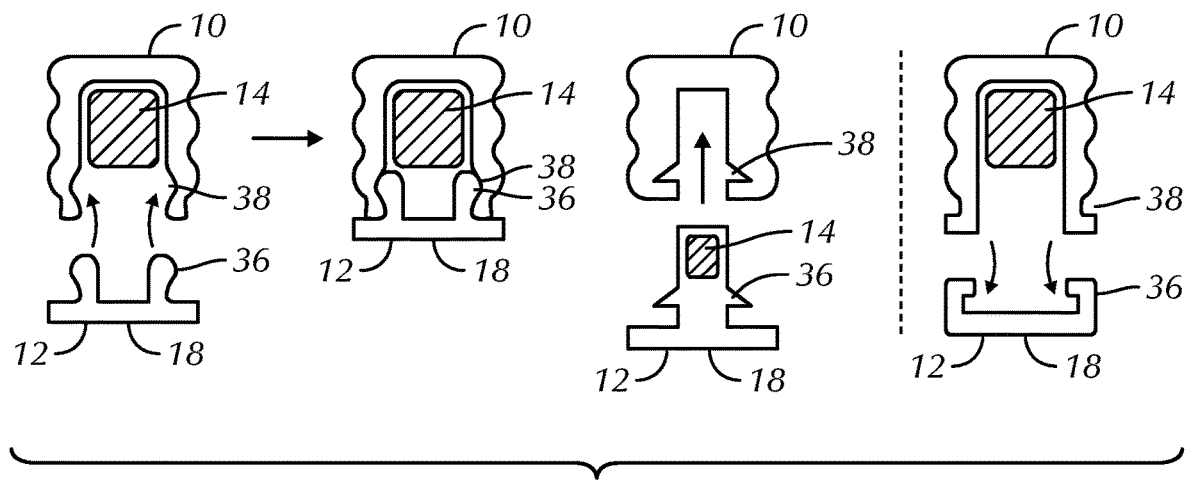
FIGS. 2A-2C illustrate various mating configurations of a piston and piston rod according to other preferred embodiments of the present invention.
Figure 2B:
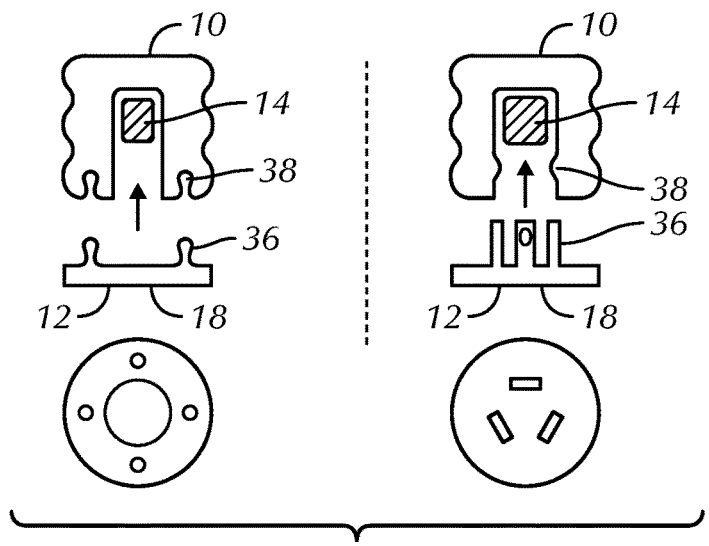
Figure 2C:
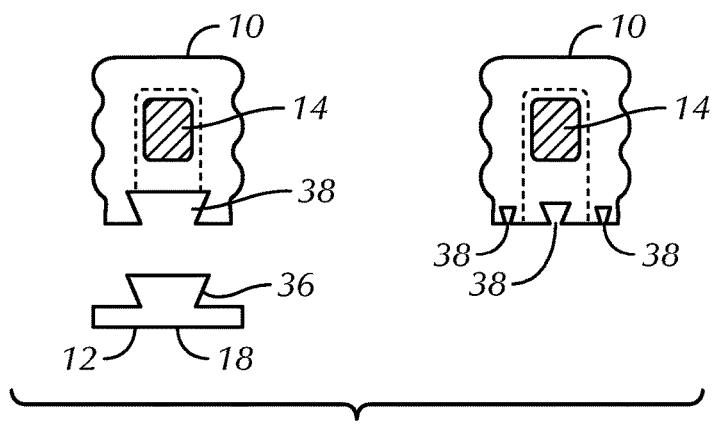

Instead of a threaded mechanical interlock, the first end 18 of the piston rod 12 and the piston 10 may be engaged with each other by any known mechanical interlock configuration. For example, referring to FIGS. 2A-2C, there are shown various exemplary embodiments of mechanical interlocks that may be utilized to connect the piston rod 12 and the piston 10 together to form the assembly 16. In particular, FIG. 2A shows various embodiments in which the first end 18 of the piston rod 12 includes an annular protrusion 36 projecting radially upwardly from the piston rod 12 and configured to engage with a corresponding annular recess 38 formed in the piston 10. FIG. 2B shows various embodiments in which the first end 18 of the piston rod 12 includes a plurality of spaced-apart protrusions 36 projecting radially upwardly from the piston rod 12 and configured to engage with corresponding spaced-apart recesses or indentations 38 formed in the piston 10. FIG. 2C shows various embodiments in which the first end 18 of the piston rod 12 includes a plurality of tapered protrusions 36 projecting radially upwardly from the piston rod 12 and configured to engage with corresponding spaced-apart recesses or notches 38 formed in the piston 10 (e.g., at a dovetail joint). It will be understood that in any of the embodiments disclosed herein, the electronic device 14 may be embedded within or attached to either the piston rod 12 or the piston 10.

Figure 4A:
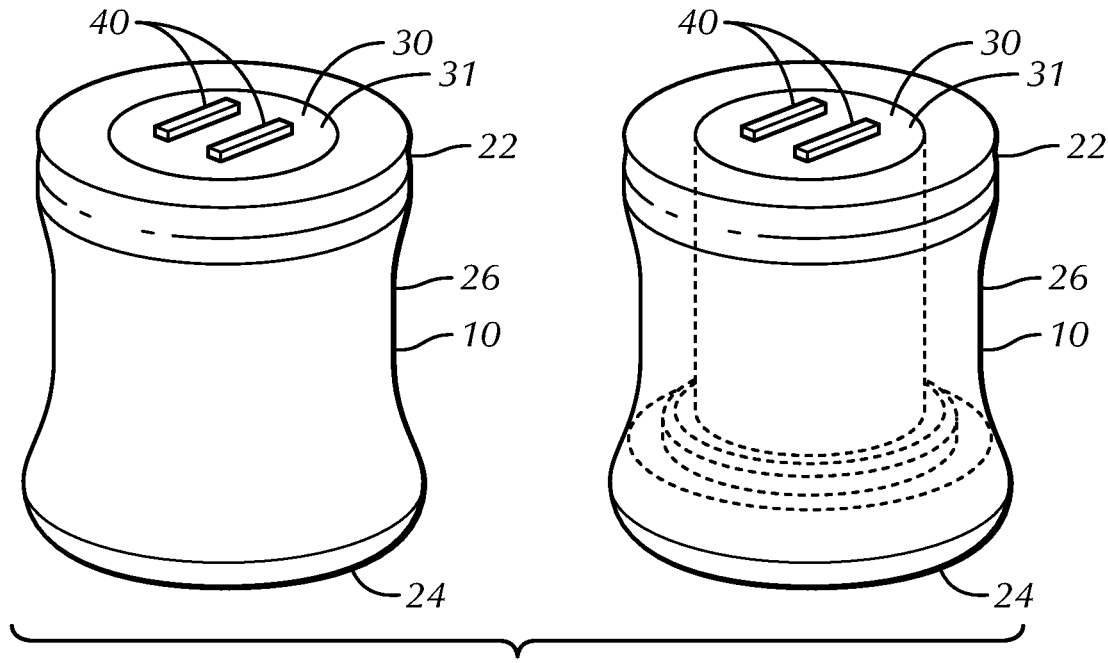
FIGS. 4A-4B illustrate various piston configurations according to other preferred embodiments of the present invention.
Figure 4B:
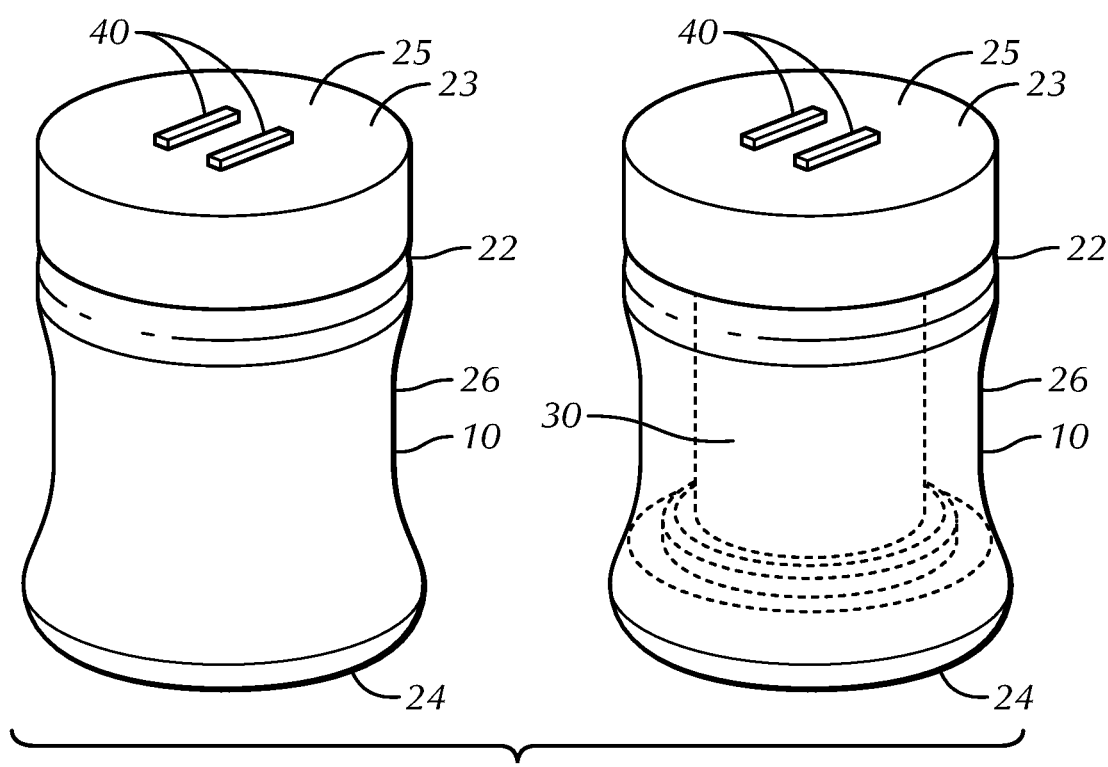

Referring to FIGS. 3A-3B, in another embodiment, the piston rod 12 and piston 10 are configured essentially the same as that of FIGS. 1A-1B and may be interlocked or engaged together in any manner as disclosed herein with respect to FIGS. 1A-1B and 2A-2C. The recess 34 of the inner cylindrical member 30 is closed off by an upper lateral wall 31. The first end 18 of the piston 12 and the lateral wall 31 of the piston 10 includes one or more corresponding exposed electrical contacts 40 (also shown in FIG. 4A) which engage each other when the piston rod 12 is engaged or interlocked with the piston 10, while the electronic device 14 remains embedded in the piston rod 12. It will be understood that while the embodiment of FIGS. 3A-3B includes the electrical contacts 40 being formed on the upper closed wall 31 of the inner cylindrical member 30, the recess 34 may remain open for receiving the piston rod 12 and the electrical contacts 40 may alternatively be formed on a lower lateral wall 31 of the inner cylindrical member 30, such that an electrical connection would be achieved when the first end 18 of the piston rod 12 is received within the recess 34 and contacts the lower lateral wall 31 of the inner cylindrical member 30 (as in the configuration of FIGS. 1A-1B). Alternatively, as shown in FIG. 4B, the open end 22 of the piston 10 may be closed off by a cylindrical body 23 having a lateral wall 25 provided with the electrical contacts 40.

Figure 5:
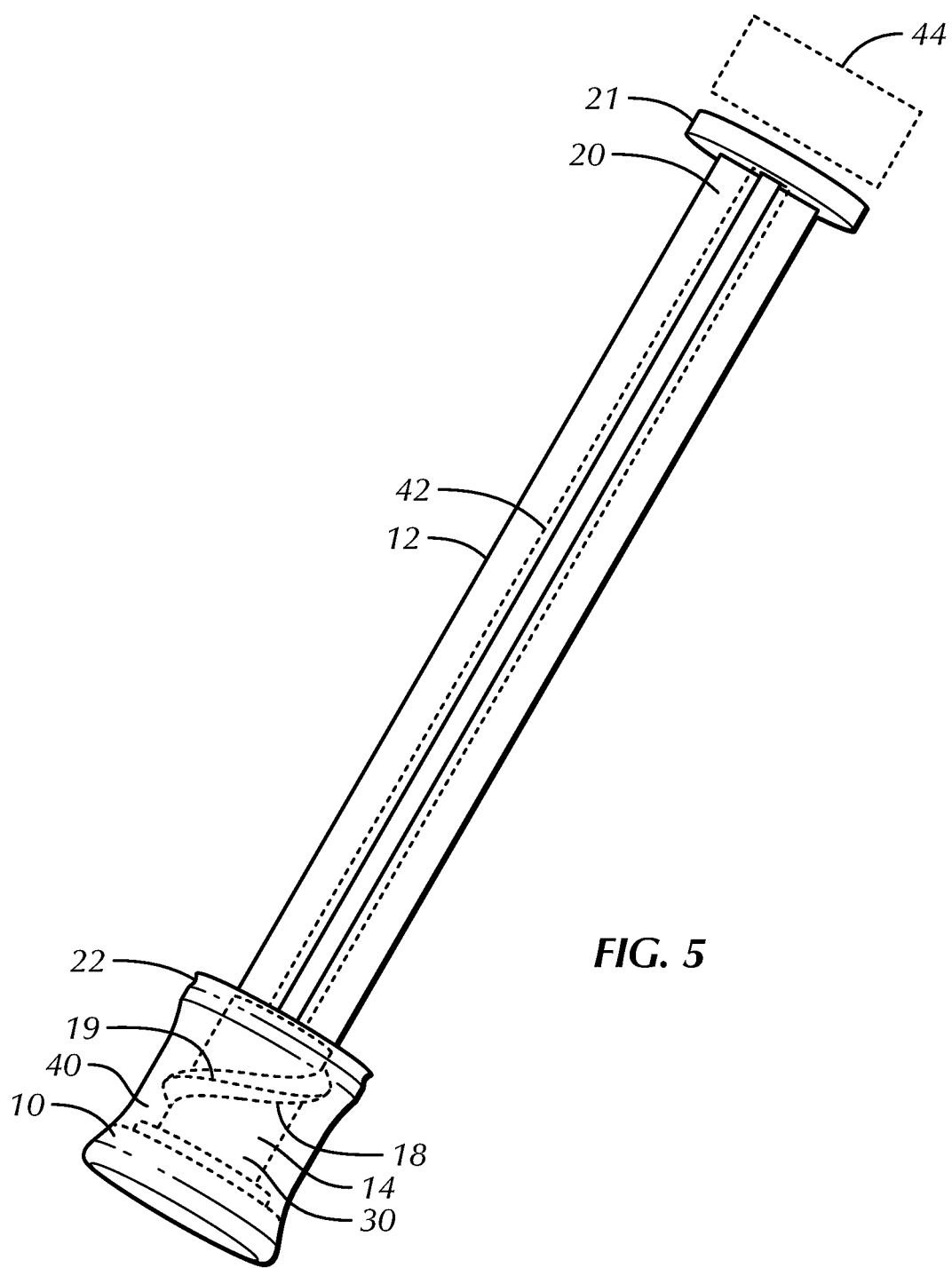
FIG. 5 is a perspective view of a piston and piston rod assembly including an embedded electronic device according to another preferred embodiment of the present invention.

In another embodiment, as shown in FIG. 5, wires 42 may extend through the body of the piston rod 12 and a battery 44 may be provided at a remote location (i.e., proximate the second end 20), so that the electronic device 14 may be powered by the remote battery 44. For example, the battery 44 may energize the electronic device 14 so that it becomes active or may even power a motor.

Figure 6:
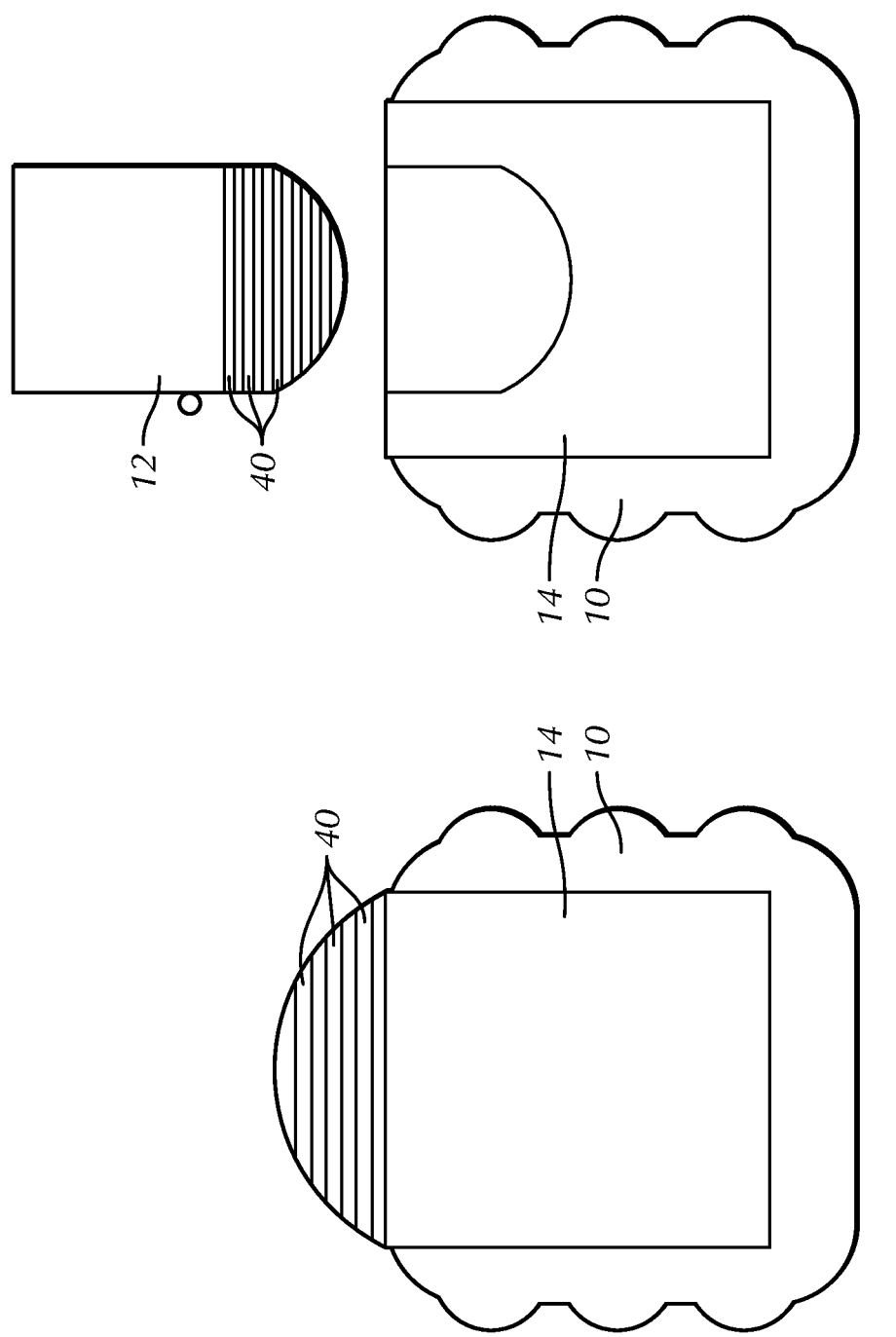
FIG. 6 illustrates piston and piston rod assemblies including an embedded electronic device and annular contacts according to another preferred embodiment of the present invention.

More particularly, the electrical contacts 40 may enable both power and data communication. With such a direct electrical communication, power transmission and/or data communication may be implemented in a more secure and robust way. The mating contacts 40 may be formed as radial or annular members configured to engage each other, as shown in FIG. 6, which also mitigates issues that may arise upon attempting to achieve alignment of the piston rod 12 and piston 10 (i.e., especially in cases where a conical, hemispherical, or other geometry is used to assist with mating). The use of multiple rotatable electronic contacts allows for ease of rotation of the piston rod 12, if necessary, and ease of assembly of the piston 10 and piston rod 12.

Figure 7:
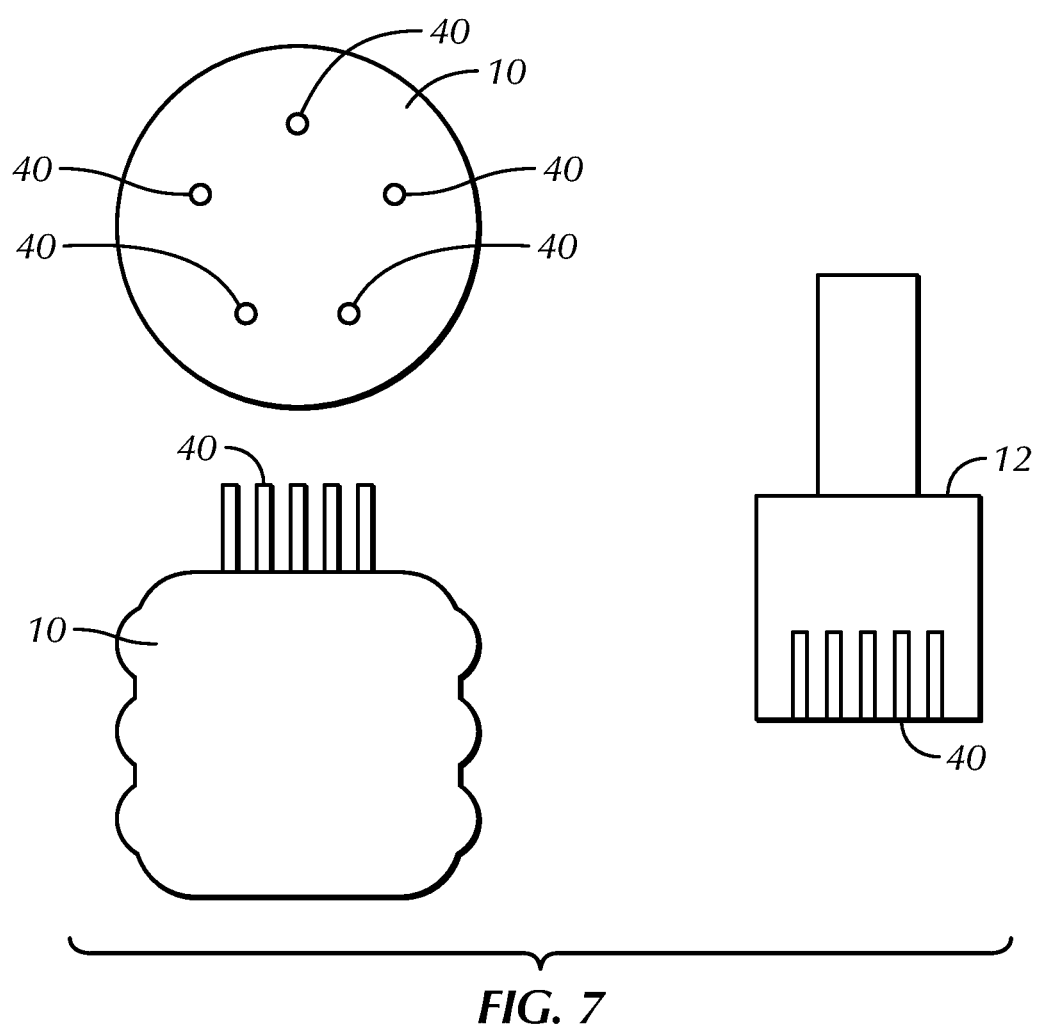
FIG. 7 illustrates a piston and piston rod assembly including an embedded electronic device and contacts in the form of pins and pin receptacles according to another preferred embodiment of the present invention.
Figure 8:
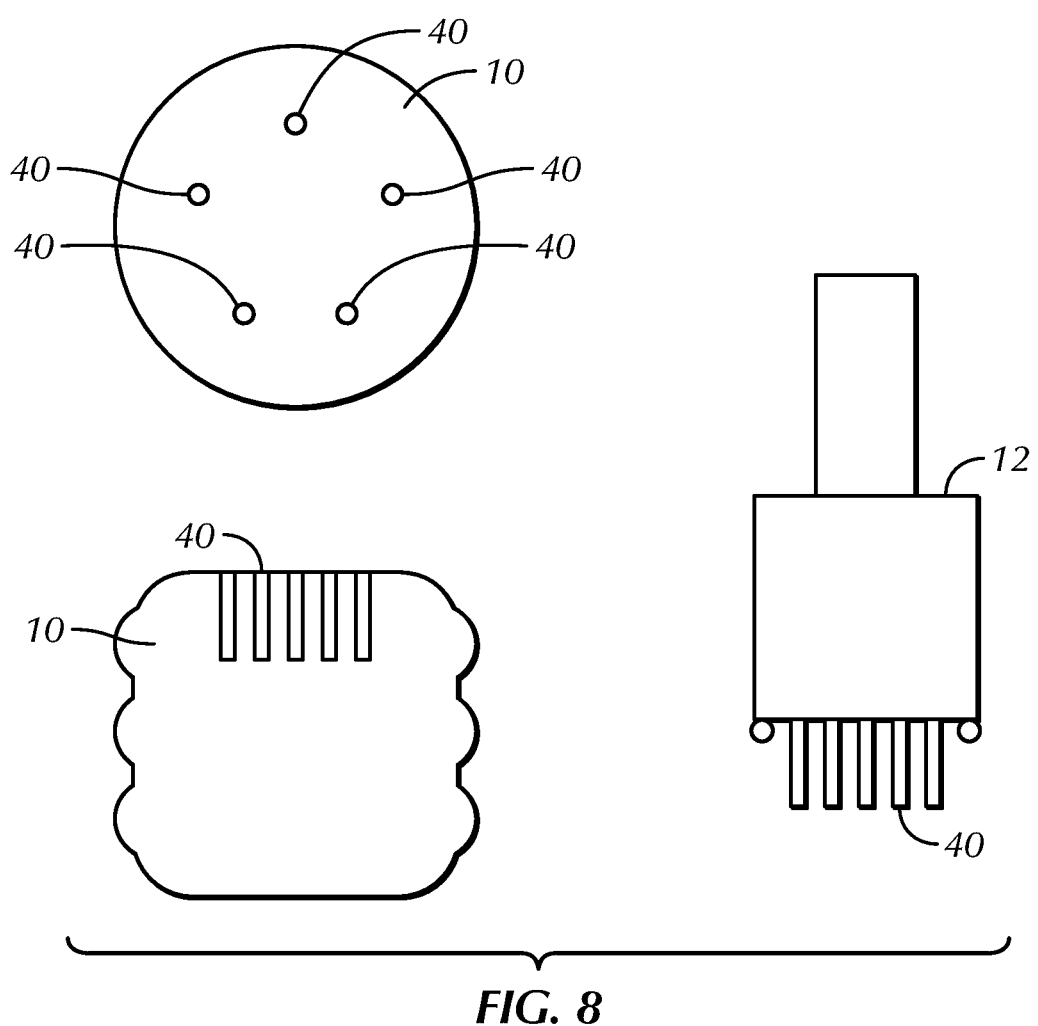
FIG. 8 illustrates a piston and piston rod assembly including an embedded electronic device and contacts in the form of pins and pin receptacles according to another preferred embodiment of the present invention.
Figure 9:
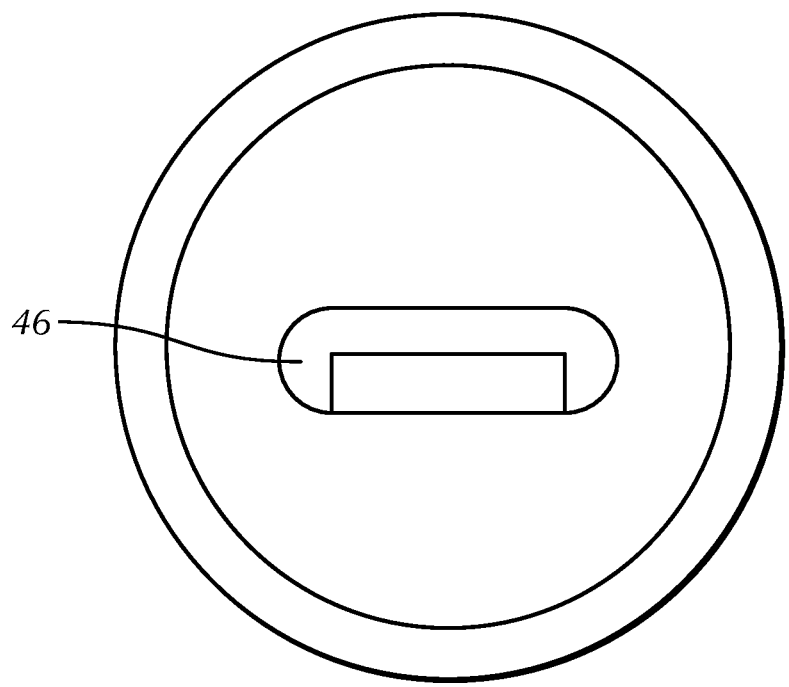
FIG. 9 is a top plan view a piston and piston rod assembly including an embedded electronic device and a USB port according to another preferred embodiment of the present invention.

It will be understood that the electrical contacts 40 may take any known form. For example, as shown in FIG. 7, the piston 10 may include a plurality of contacts 40 in the form of pins and the piston rod 12 may include a plurality of mating contacts 40 in the form of pin receptacles. Alternatively, as shown in FIG. 8, the piston rod 12 may include a plurality of contacts 40 in the form of pins and the piston 10 may include a plurality of mating contacts 40 in the form of pin receptacles. In other embodiments, as shown in FIG. 9, a plug or connector 46 may be included to enable communication and power transmission between the piston 10 and piston rod 12. In any of these embodiments, an optional sealing element (e.g., an O-ring) may be utilized for protection of the drug product or contacts 40 (i.e., by creating a hermetic seal).

The electrical contacts 40 and associated wires 42 also eliminate wireless communication which, in turn, prevents the possibility of interference, allows for greater power transmission with power losses, and makes tampering/spoofing of the signals more difficult. For example, avoiding wireless transmission could assist with ensuring patient privacy.

In one embodiment, the assembly includes the battery 44, a processor, and a transmitter, such that the assembly is configured to sense a signal (e.g., through the battery-powered sensor) and either process the signal as a feedback to control the medical device (e.g. to increase or decrease dosage rate, stop dosage, and the like), or send a signal to a smartphone or other external device that either monitors the signal or receives the signal, processes it, and then adjusts movement of the actuator of the medical device accordingly.

For example, the assembly may include a controller configured to receive data associated with an administered dose of the injectable medicine, and assess whether the administered dose meets one or more prescribed parameters. The controller may also be configured to adjust a subsequent dose of the injectable medicine to be administered based on the assessment. More particularly, the controller may be configured to receive data associated with the dose of the injectable medicine, assess whether the dose has been taken at the prescribed time and on the prescribed day, and transmit an adjusted dose and instruction to administer the dose based on the assessment.

It will be understood by those skilled in the art that the electrical connection may be achieved by mechanisms other than electrical contacts 40 as described herein. For example, an electrical connection may be achieved by one of the piston 10 and piston rod 12 including a USB port, while the other of the piston 10 and piston rod 12 includes a corresponding USB connector. Alternatively, for example, the piston 10 and piston rod 12 may be provided with corresponding helical threads configured to mate with each other, each of which is formed as or includes an electrical contact.

The electronic device or package 14, according to any of the embodiments described herein, may incorporate sensing technology, such as sensors to measure/detect the temperature of medical device/component itself or the surrounding environment, the pressure within the medical device, the differential pressure across the assembly 16, and more particularly the piston 10, which may occur, for example, by gas generation within the container due to drug breakdown, the capacitance for liquid level or the piston position, or light exposure for photosensitive drugs. The electronic device or package 14, according to any of the embodiments described herein, may also incorporate tracking technology, such as electronics to identify information encoded in an EEPROM or NFC chip. The device 14 may contain a serial number or expiration date, and may be traceable, for example, to determine whether or not a drug is under recall. The device 14 may also be used to confirm that the assembly 16 is an official product, rather than a third party grey market copy or other counterfeit. The device 14 may also be used, for example, by an RFID check to ensure that the assembly 16 is an appropriate delivery device for the drug to be dispensed. The device 14 may also be used to control the dispensing of the drug from the assembly 16 and to update inventory levels automatically.

The electronic device or package 14, according to any of the embodiments described herein, may also incorporate measurement technology, such as for measuring or detecting the location of a piston during use and/or the speed of delivery of the drug (e.g., by monitoring the piston rate of movement), or for providing feedback about when a piston reaches a pre-set dosage point (for example, the device 14 may be used to drive haptic feedback in the assembly 16). In cases where the piston 10 is a replaceable component, the electronic device 14 may be used to determine when the replacement should occur or if drug exposure should be limited. The electronic device 14 may also be used to detect tampering. For example, the device 14 may include a resistive foil whose value changes if it is punctured by a needle.

The electronic device or package 14, according to any of the embodiments described herein, may also incorporate various other types of technology. For example, the device 14 may incorporate muscle wire (flexinol or Shape Memory Actuator Wire) technology in the shape of a coil coupled to the electronic device 14. When a current flows throw the muscle wire, the muscle wire contracts. Such functionality could be used, for example, to tense/relax the piston 10, in order to make it easier or more difficult to move. The device 14 may also incorporate piezo technology (including, but not limited to, PVDF which is a piezoelectric material or a piezoelectric device) to agitate the drug contained in the medical component 10 prior to use. Another possible use of the electronic device 14 is to actuate induction heating to heat the drug contained in the medical device (e.g., syringe) prior to use, or to effect intentional spoiling of the drug if a tampering or misuse alarm is triggered or if a patient is attempting to dispense the drug after its expiration date. The electronic device 14 may also enable electrical contact between the piston 10 and the actuating rod to supply power to the piston electronics and confirm if the drug contained in the medical device is correct, monitor the date, etc., as disclosed herein.

The present invention may also encapsulate other materials, besides an electronic device 14, inside of the assembly 16. For example, instead of the electronic device 14, the piston 10 and/or piston rod 12 may include an incompressible material embedded therein to change the mechanical properties of the component 10, 12. Alternatively, the piston 10 and/or piston rod 12 may include a dense material embedded therein to change the weight of the component 10, 12, for example, for purposes of gravity or acceleration induced operation. Alternatively, the piston 10 and/or piston rod 12 may include a magnet or a magnetic material embedded therein, such that the magnet or magnetic material is configured to interact with external sensors or magnetic packaging.

As noted above, the electronic device 14 may be embedded in the first or second component (e.g., the piston 10 or the piston rod 12) by any known method. For example, referring to FIGS. 10A-11E, there are shown various embodiments of methods of manufacturing a medical component 210 utilizing a mold 214 and an elastomer sheet 216 in a one-step molding process, and more particularly in a one-step compression molding process. The mold 214 includes an upper mold half 215 having an open cavity 215a and a lower mold half 217 having an open cavity 217a. Each cavity 215a, 217a is preferably an open heated mold cavity 215. In a preferred embodiment, the mold 214 includes a plurality of upper and lower mold halves 215, 217 and respective cavities 215a, 217a arranged in an array.

The elastomer sheet 216 is preferably formed of one or more elastomeric materials (i.e., one or more of the elastomeric materials described above) in a partially cured stage. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes. As such, the elastomer sheet 16 is essentially an elastomer preform. The elastomer sheet 216 has a first surface 219 and an opposing second surface 221.

Figure 10A:
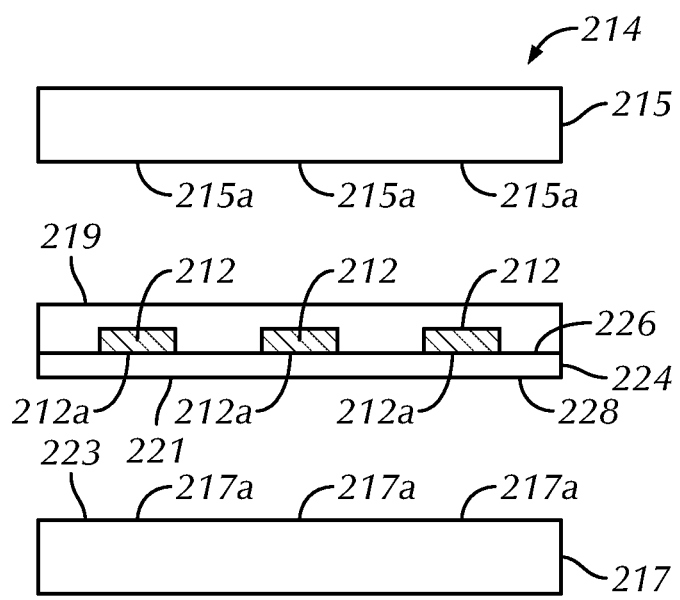
FIGS. 10A-10B illustrate a method of manufacturing a medical component in a one-step molding process according to a preferred embodiment of the present invention.
Figure 10B:
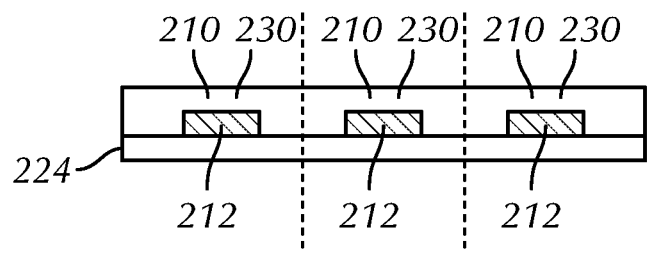

In the embodiment of FIGS. 10A-10B, the bottom surface of the mold cavity 217a of the lower mold half 217 defines a planar surface 223. The planar surface 223 also corresponds to the interior bottom surface of the lower mold half 217. The elastomer sheet 216 includes at least one electronic device 212 arranged or embedded therein. More particularly, the electronic device 212 is positioned within the elastomer sheet 216 such that an exposed or distal surface 212a of the electronic device 212 is flush with the second surface 221. In a preferred embodiment, the elastomer sheet 216 comprises a plurality of electronic devices 212 arranged in an array that corresponds to the array of mold cavities 215a, 217a.

In the embodiment of FIGS. 10A-10B, the elastomer sheet 216 further comprises a protective or barrier film 224 on the side of the second surface 221. The protective film 224 has a first surface 226 and an opposing second surface 228. The protective film 224 is provided so as to cover the exposed surface 212a of each electronic device 212, such that the first surface 226 of the protective film 224 is in direct contact with the exposed surface 212a of each electronic device 212. It will be understood that the protective film 224 may be provided only in the areas of the electronic devices 212 or so as to cover the entire second surface 221 of the elastomer sheet 216.

In the manufacturing method according to the embodiment of FIGS. 10A-10B, the elastomer sheet 216 is positioned over the lower mold half 217, such that the position of each electronic device 212 aligns with the positon of a respective open mold cavity 217a. In the assembled position, the second surface 228 of the protective film 224 is in contact, and more particularly, direct contact with the planar surface 223. Each electronic device 212 is preferably held in place within the mold cavity 217a by vacuum assist. The assembly is then subjected to compression molding to fully cure the elastomeric material. More particularly, the mold 214 is closed such that each upper mold half 215 covers each respective lower mold half 217, and heat and pressure are applied to cause the elastomeric material of the elastomer sheet 216 to flow, thereby forcing the flowing elastomeric material into contact with all areas of each mold cavity 215a, 217a until the elastomeric material has cured to form the medical component 210.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

The resulting cured form includes one electronic device 212 per each mold part. Each resulting medical component 210 comprises an electronic device 212 fully encapsulated by the cured elastomeric material 230 and the protective film 224. The protective film 224 may be any polymer or ceramic film that would enable an electrical or optical path to the electronic device 212, but still provide barrier properties for encapsulation of the electronic device 212. In a preferred embodiment, the protective film 224 is a fluoropolymer film. Preferably, the fluoropolymer film 224 is provided on the surface of the medical component 210 which is configured to contact the pharmaceutical medicament (i.e., the interface or contact surface).

Fluoropolymers are readily known in the art and a detailed description of them is not necessary for a complete understanding of the present invention. Exemplary fluoropolymers include, but are not limited to, polytetrafluoroethylene (PTFE), homopolymers and copolymers of tetrafluoroethylene (TFE), perfluoroalkoxy polymer resin (PFA), copolymers of hexafluoropropylene and tetrafluoroethylene, polyethylenetetrafluoroethylene (PETFE), polyvinyl fluoride (PVF), fluorinated ethylenepropylene copolymers (FEP), polyethylenechlorotrifluoroethylene (PECTFE), polyvinylidene fluoride (PVDF), polychlorotrifluoroethylene (PCTFE), and derivatives thereof. Preferably, the protective film 224 is formed of FluoroTec®.

In the embodiment of FIGS. 11A-11E, the bottom surface 223 of the cavity 217a of each lower mold half 217 is recessed so as to be spaced apart from the elastomer sheet 216 in the assembled position. As such, during compression molding, the elastomeric material of the elastomer sheet 216 is able to flow into the space between the sheet 216 and the bottom surface 223, such that the electronic device 212 is fully encapsulated by the elastomeric material. As such, in the embodiments of FIGS. 11A-11E, the elastomer sheet 216 need not include the protective film 224.

Figure 11A:
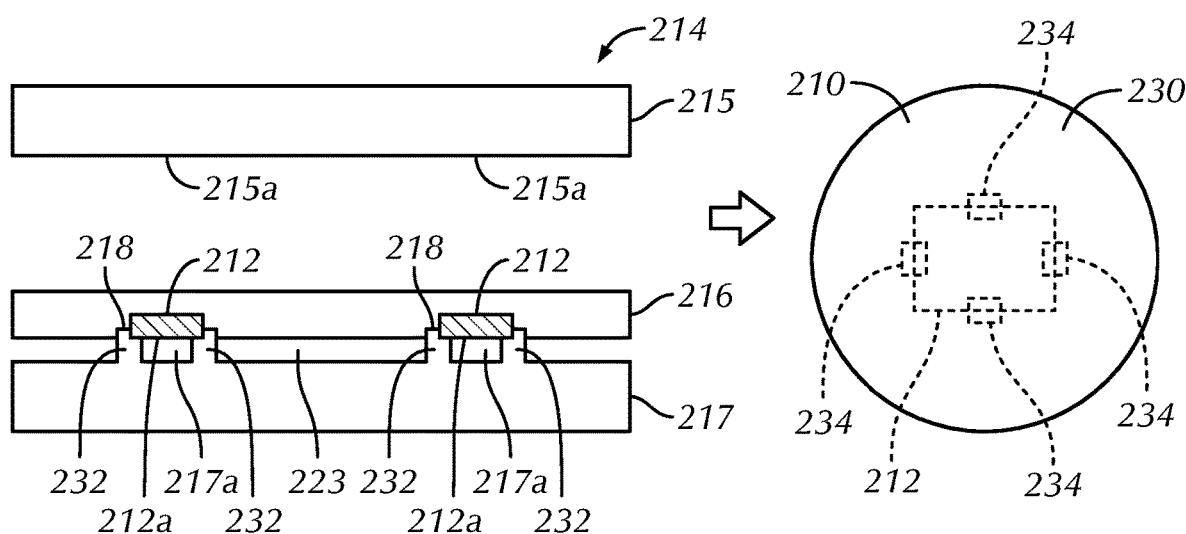

In the embodiment of FIG. 11A, each lower mold half 217 includes at least one protrusion 232, and more preferably a plurality of protrusions 232, for holding the electronic device 212 in place within the mold cavity 217a during the compression molding process, for example, to keep the electronic device 212 centered. More particularly, the plurality of protrusions 232 form a pedestal 218 upon which the elastomer sheet 216, and more particularly the electronic device 212, rests during compression molding, such that the exposed surface 212a of the electronic device 212 is spaced apart from the bottom surface 223 of the cavity 217a. As such, during compression molding, the electronic device 212 is held securely in place and the elastomeric material may flow into the space between the electronic device 212 and the bottom surface 223, such that the electronic device 212 is fully encapsulated by the elastomeric material in the finished medical component 210. As a result of the interaction between the pedestal 218 and the elastomer sheet 216 during the compression molding process, the finished medical component 210 may include a plurality of indentations or voids 234 in positions corresponding to the location of the distal ends of the protrusions 232 of the pedestal 218.

Figure 11E:
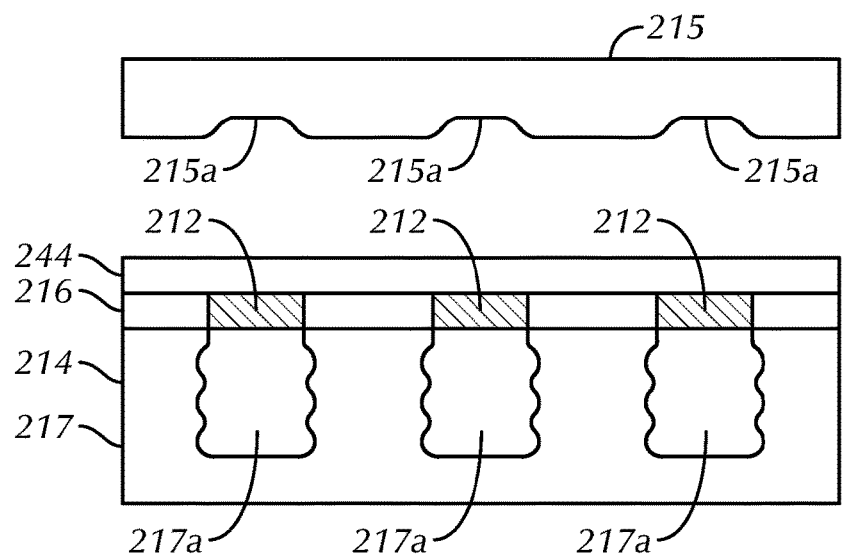
Figure 11B:
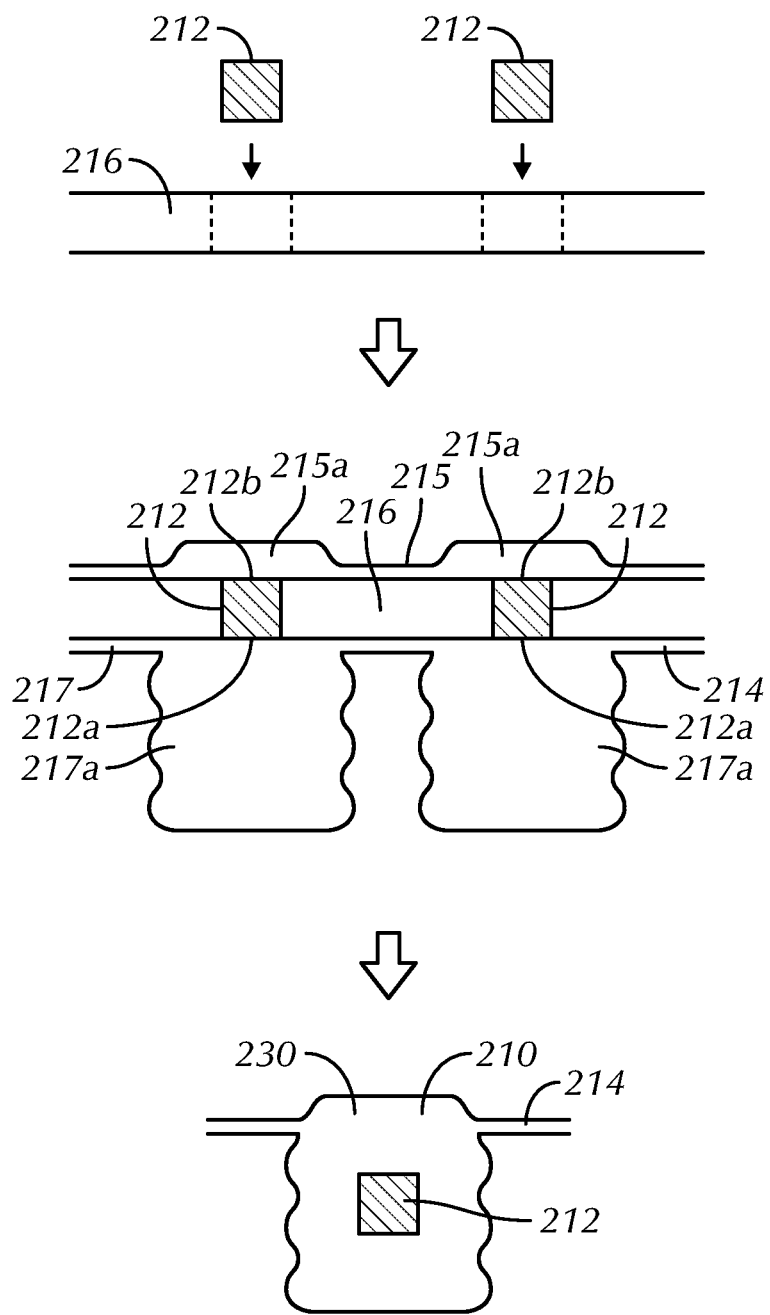

In the embodiment of FIG. 11B, the plurality of electronic devices 212 are embedded in the elastomer sheet 216, such that both the opposing distal and proximal surfaces 212a, 212b of the device 212 are exposed. The open cavities 215a, 217a of the mold halves 215, 217 are recessed in the respective walls of the mold halves 215, 217, such that during compression molding, the elastomeric material flows all around the electronic device 212, thereby ensuring that the electronic device 212 is fully encapsulated by the elastomeric material in the finished medical component 210.

In one variation, shown in FIG. 11E, the elastomeric sheet 216 is subjected to freezing temperatures (i.e. is frozen) before being positioned in the mold 214. This enables the sheet 216 to better hold its shape for a portion of the cure cycle and also allows for superior control in the placement of the encapsulated electronic devices 212 during the one-step molding process. The frozen elastomer sheet 16 is then positioned over the lower mold half 217, such that the position of each electronic device 212 aligns with the positon of a respective open mold cavity 217a. The bottom surface of the cavity 217a of each lower mold half 217 is recessed so as to be spaced apart from the elastomer sheet 216 in the assembled position.

Next, a second elastomer sheet 244 is positioned over the frozen elastomer sheet 216. However, the second elastomer sheet 244 has not been frozen. Thus, during the molding process (e.g., compression molding), the elastomeric material of the second sheet 244 flows faster than that of the frozen sheet 216, allowing for better control of the alignment of the electronic devices 212 during the compression molding. The elastomeric material of both elastomer sheets 216, 244 is able to flow into the spaces of each open mold cavity 215a, 217a, such that each electronic device 212 is fully encapsulated by the elastomeric material. It will be understood that the first and second sheets 216, 244 may be formed of the same elastomeric material or different elastomeric materials.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In the embodiment of FIG. 11C, the lower mold half 217 includes a protrusion 236 that mates with a corresponding indentation 238 formed in the electronic device 212, in order to hold the electronic device 212 in position during compression molding. The protrusion 236 is thus an alignment pin. In another embodiment, the protrusion 236 and the indentation 238 may be provided with mating threads. Again, the open cavities 215a, 217a of the mold halves 215, 217 are recessed in the respective walls of the mold halves 215, 217, such that during compression molding, the elastomeric material flows all around the electronic device 212, thereby ensuring that the electronic device 212 is fully encapsulated by the elastomeric material in the finished medical component 210.

FIG. 11D depicts an embodiment in which the electronic device 212 includes a protrusion 240 that mates with a corresponding indentation 242 formed in the wall of the lower mold half 217. The body of the electronic device 212 is embedded within the elastomer sheet 216, similar to FIG. 11B, while the protrusion 240 extends outwardly away from the sheet 216. In another embodiment, the protrusion 240 and the indentation 242 may be provided with mating threads. Again, the open cavities 215a, 217a of the mold halves 215, 217 are recessed in the respective walls of the mold halves 215, 217, such that during compression molding, the elastomeric material flows all around the electronic device 212, thereby ensuring that the electronic device 212 is fully encapsulated by the elastomeric material in the finished medical component 210.

Referring to FIGS. 12A-12H, there is shown an embodiment of a method of manufacturing the medical component 210 utilizing an elastomer tube 116 in a one-step molding process. The molding process may be any known molding process (e.g., compression molding, injection molding and the like). The elastomer tube 116 is preferably formed of one or more elastomeric materials (i.e., one or more of the elastomeric materials described above) in an uncured or partially cured (i.e., semi-cured) state. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

The elastomer tube 116 is essentially an elastomer preform. The elastomer tube 116 is generally cylindrical with a hollow interior 123, and has a first end 119 and an opposing second end 121. The portion of the tube 116 including the first end 119 is hereinafter referred to as a first half of the tube 116 and the portion of the tube 116 including the second end 121 is hereinafter referred to as a second half of the tube 116.

Figure 12A:
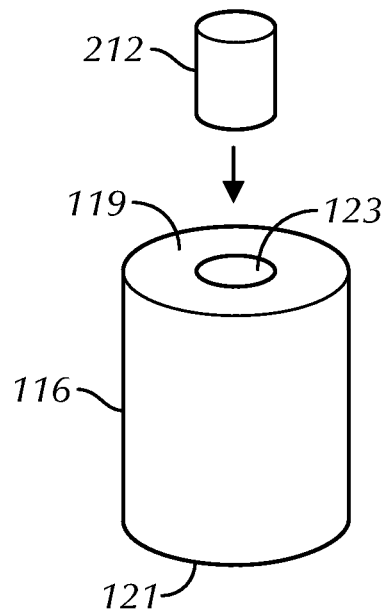
FIGS. 12A-12H schematically illustrate a method of manufacturing a medical component in a one-step molding process according to another preferred embodiment of the present invention.
Figure 12B:
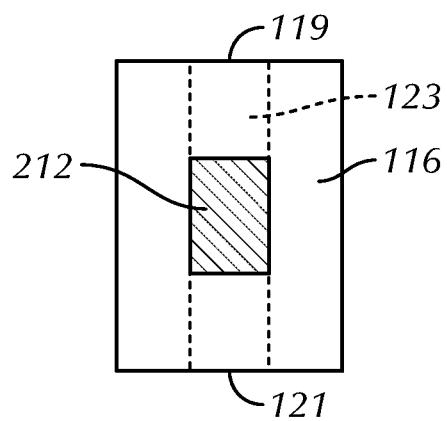
Figure 12C:
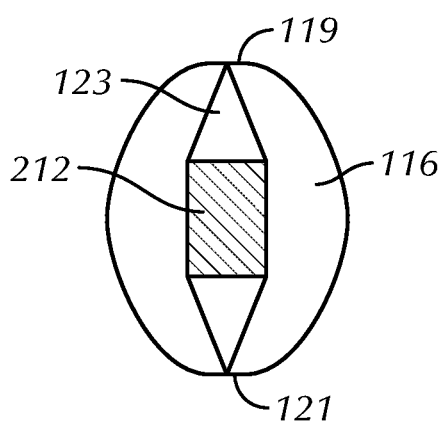
Figure 12D:
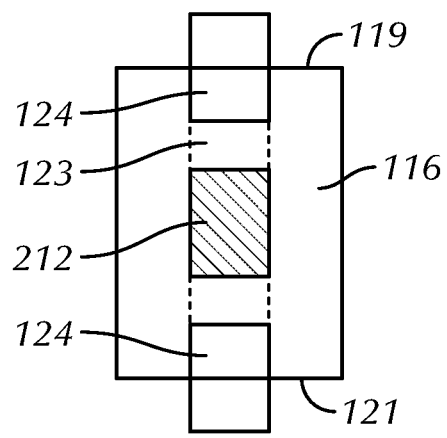
Figure 12E:
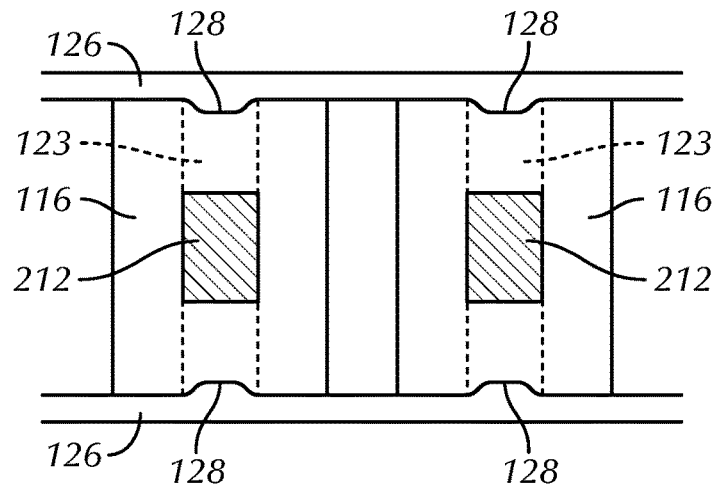
Figure 12F:
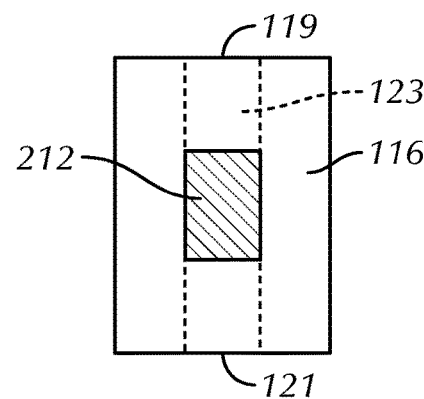

After the uncured or semi-cured elastomer tube 116 is formed, one or more electronic devices 212 is positioned within the hollow interior 123 of the tube 116. Next, one of various processes may be carried out to secure the electronic device 212 in place. For example, as shown in FIG. 12C, both the first and second halves of the tube 116 may be crimped or pinched together while the elastomeric material is still soft, pliable and tacky so as to maintain the electronic device 212 in place. Alternatively, as shown in FIG. 12D, extruded elastomeric rods or plugs 124 may be positioned in the hollow interior 123 in the first and second halves (i.e., on either side of the electronic device 212) to secure the electronic device 212 in place. Alternatively, as shown in FIG. 12E, preformed elastomeric sheets 126, each of which includes one or more protrusions 128, may be positioned on either end 119, 121 of the tube 116, such that the protrusions 128 are received within the hollow interior 123 of the tube 116, thereby securing the electronic device 212 in place. Alternatively, no further processes are necessary, as shown in FIG. 12F, if the electronic device 212 has already sufficiently secured itself within the hollow interior 123 (e.g., due to its size). It will be understood by those skill in the art that a combination of the aforementioned processes of FIGS. 12C-12F may be carried out. For example, the process of FIG. 12C may be used on the first half of the tube 116, while the process of FIG. 12D is used on the second half of the tube 116.

Figure 12G:
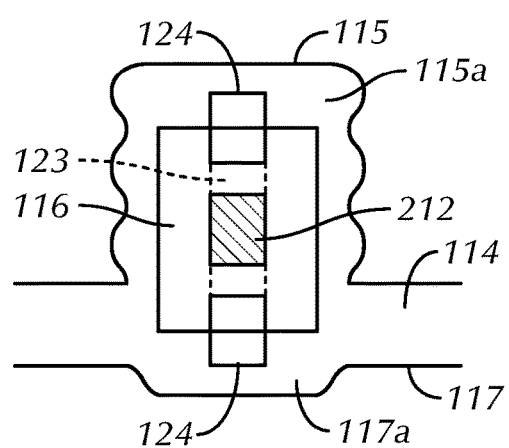
Figure 12H:
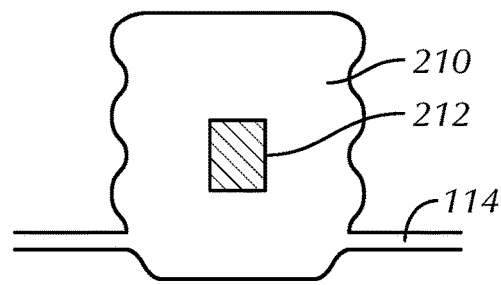

Finally, as shown in FIGS. 12G-12H, the uncured or semi-cured elastomeric tube 116 with the electronic device 212 secured therein is placed within a mold 114 and heat and pressure are applied to cause the elastomeric material of the elastomer tube 116 to flow, and the flowing elastomeric material fills any voids (i.e., in the hollow interior 123) while maintaining the center of the electronic device 212 (see FIG. 3H). The molding process is carried out under predetermined time, heat and pressure conditions, until the elastomeric material has cured to form the medical component 210.

The mold 114 includes an upper mold half 115 having an open cavity 115a and a lower mold half 117 having an open cavity 117a. Each cavity 115a, 117a is preferably an open heated mold cavity 115. In a preferred embodiment, the mold 114 includes a plurality of upper and lower mold halves 115, 117 and respective cavities 115a, 117a arranged in an array. As such, a plurality of semi-cured elastomeric tubes 116 with electronic devices 212 secured therein may be simultaneously compression molded to form the medical components 210.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 13A:
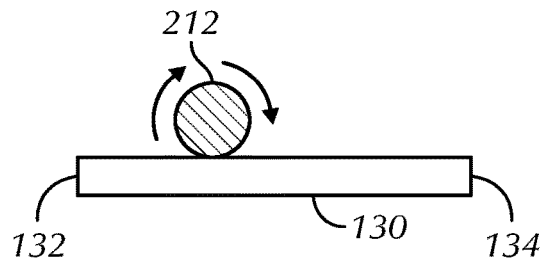
FIGS. 13A-13C schematically illustrate a method of manufacturing a medical component in a one-step molding process according to another preferred embodiment of the present invention.
Figure 13B:
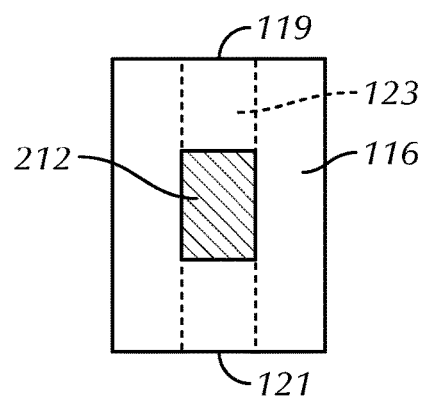
Figure 13C:
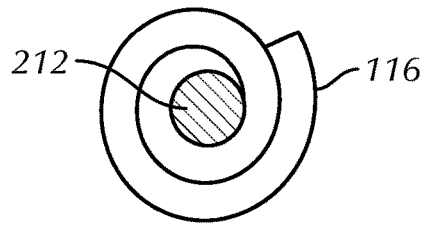

Referring to FIGS. 13A-13C, there are shown alternative embodiments for preparing the uncured or semi-cured elastomeric tube 116 and electronic device 212 assembly. Specifically, referring to FIG. 13A, an uncured or semi-cured elastomeric sheet 130 may be formed in a molding step/process under predetermined time, heat and pressure conditions. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

The sheet 130 is a generally planar and flat sheet having a first end 132 and an opposing second end 134. The electronic device 212 is placed on the flat surface of the sheet 130 proximate the first end 132, and more particularly proximate a geometric center of the first end 132. Then, the first end 132 of the sheet 130 is rolled over the electronic device 212 and continues to be rolled toward the second end 134. As such, the sheet 130 is wrapped around the electronic device 212, thereby forming the uncured or semi-cured elastomer tube 116 having an electronic device 212 positioned within a center of the hollow interior 123 of the tube 116, as shown in FIGS. 13B-13C. Next, the tube 116 and electronic device 212 are subjected to the securing and molding processes described above with respect to FIGS. 12A-12H in order to form the medical component 210.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 14A:
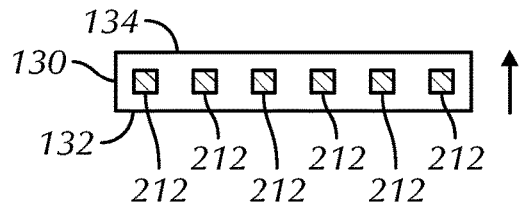
FIGS. 14A-14C schematically illustrate a method of manufacturing a medical component in a one-step molding process according to another preferred embodiment of the present invention.
Figure 14B:
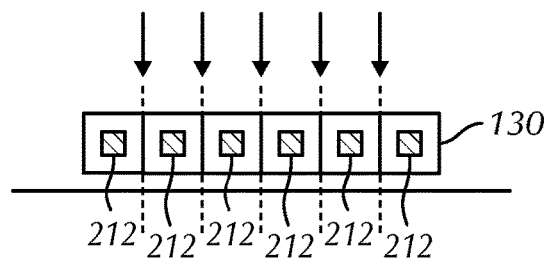
Figure 14C:
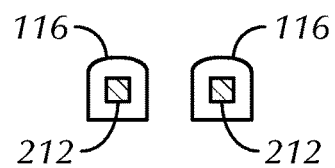

Alternatively, as shown in FIGS. 14A-14C, multiple tubes 116 may be formed simultaneously. Specifically, a plurality of electronic devices 212 are placed on the surface of the semi-cured elastomeric sheet 130 proximate the first end 132 at spaced-apart intervals (see FIG. 14A). Next, the sheet 130 is rolled over and wrapped around the electronic devices 212 in the same manner as described herein with respect to FIG. 13A. Next, referring to FIGS. 14B-14C, the sheet 130 is cut at the intervals separating the electronic devices 212, thereby forming a plurality of semi-cured elastomer tubes 116, each tube 116 having an electronic device 212 positioned within a center of its hollow interior 123. Finally, each tube 116 and electronic device 212 is subjected to the securing and molding processes described above with respect to FIGS. 12A-12H, under the aforementioned time, heat and pressure conditions, in order to form a plurality of medical components 210.

Figure 15:
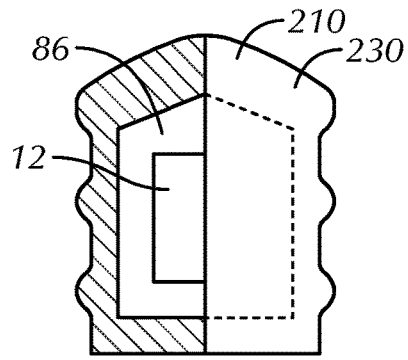
FIG. 15 illustrates a medical component including an electronic device embedded therein according to another preferred embodiment of the present invention.
Figure 16:
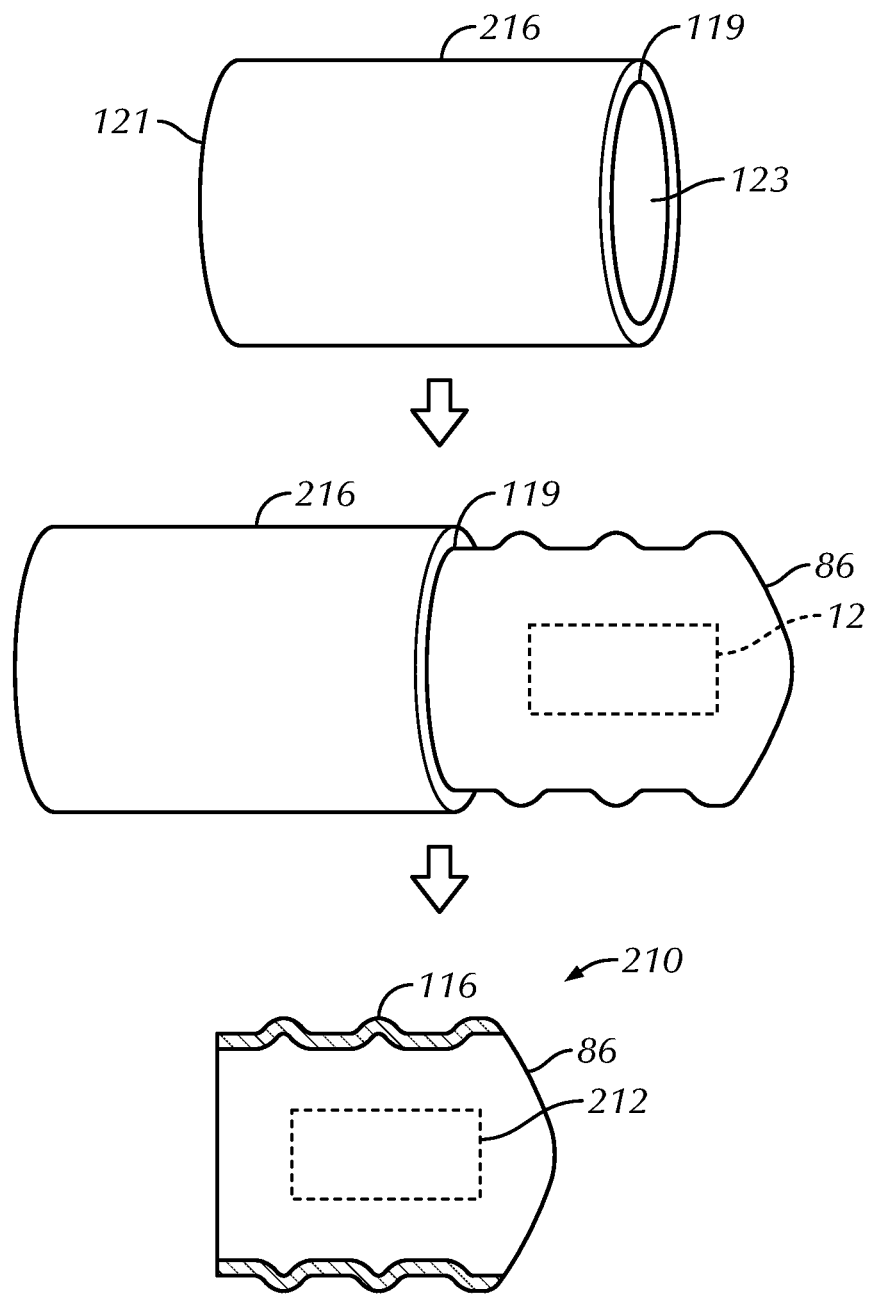
FIG. 16 schematically illustrate a method of manufacturing a medical component according to another preferred embodiment of the present invention.
Figure 17:
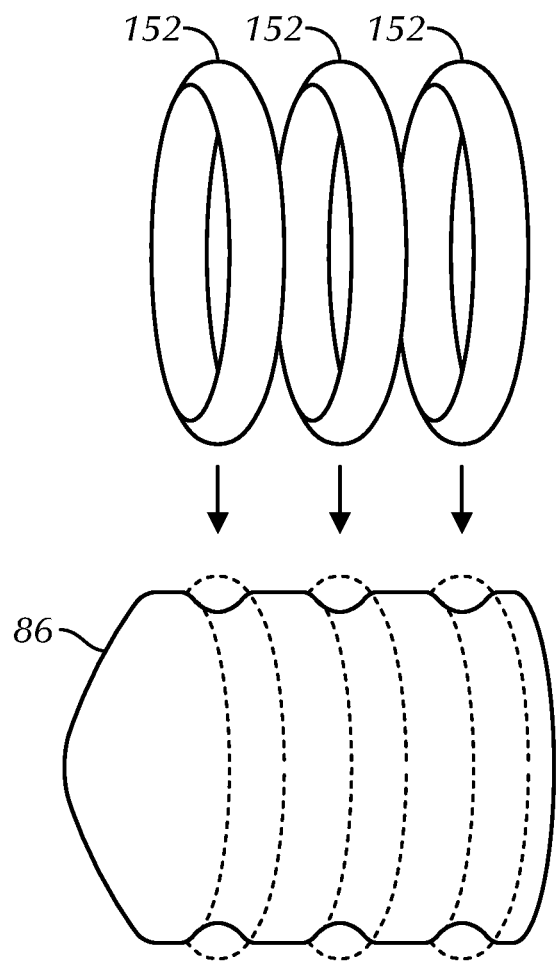
FIG. 17 schematically illustrate a method of manufacturing a medical component according to another preferred embodiment of the present invention.

Referring to FIG. 15-17, there are shown further embodiments of a method of manufacturing the medical component 210 in a one-step molding process (e.g., compression molding, injection molding, overmolding and the like). Specifically, the electronic device 212 is initially embedded within a form or receptacle 86 formed of a temperature resistant and resilient material. More particularly, the form 86 is preferably formed of a thermally stable material. For example, the form 86 may be formed of materials including, but not limited to, a ceramic material, including but not limited to alumina or silicates (e.g., quartz, porcelain or glass); a metallic material including but not limited to stainless steel, titanium, aluminum and/or anodized aluminum; or a polymer material including, but not limited to polyamides, fluoropolymers including but not limited to polytetrafluoroethylene (PTFE) or glass filed PTFE, or a polyaryletherketone (PAEK) including but not limited to polyetherketoneketone (PEKK), polyetherketone (PEK), polyetherketoneetherketoneketone (PEKEKK) and polyether ether ketone (PEEK). In one embodiment, the form 86 may comprise insulated materials, such as foam or aerogel for thermal insulation or a high temperature resistant polymer for electrical isolation of the electronic device 212. Such a material would have various advantages. For example, in the case of providing thermal insulation, cryogenic storage could be used to minimize the time the electronic device 212 is exposed to high temperature. Also, a mechanically robust form 86 is preferred, such that particularly fragile or sensitive electrical devices 212, such as microelectromechanical systems or shock/acceleration sensors, may be used.

Preferably, the form 86 is of a size and shape that corresponds to the desired size and shape of the medical component 210 to be formed.

Next, in one embodiment, as shown in FIG. 15, the form 86 provided with the electronic circuit 212 is placed in a mold and the elastomeric material 230 is overmolded onto the form 86, under predetermined time, heat and pressure conditions, in order to form the medical component 210 comprising the elastomeric material 230. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In one variation, for example where the form 86 is formed of a metallic material, the mold may be provided with a magnetic material (not shown) to facilitate accurate positioning and placement of the form 86 during molding.

In another embodiment, as shown in FIG. 16, an uncured or semi-cured elastomeric tube 116, and more particularly an uncured or semi-cured monolithic elastomeric tube 116, as described above, is formed and the form 86 provided with the electronic circuit 212 is inserted into the hollow interior 123 of the tube 116. More particularly, the tube 116 is stretched over the exterior surface of the form 86 and is mechanically formed onto the form 86. Subsequently, the assembly is subjected to the application of heat and pressure to cure and shrink-wrap the elastomeric material of the tube 116 onto the form 86. For example, a bladder type molding process may be employed to thermoform the elastomeric material of the tube 116 around the hard body of the form 86 and to provide a sufficiently smooth surface for sealability.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Alternatively, a process may be employed wherein the elastomeric material of the uncured or semi-cured elastomeric tube 116 is compressed and simultaneously rolled against a smooth surface or wheel to impart specific surface characteristics.

In one variation of the embodiment of FIG. 16, sealing elements (not shown), such as O-rings, may be utilized during the heating step, in order to ensure that the elastomeric material of the uncured or semi-cured elastomeric tube 116 is completely sealed onto the form 86. In one embodiment, the elastomeric material of the tube 116 is hermetically sealed onto the form 86 so as to provide additional barrier properties by fully enclosing any impurities associated with the material used to form the form 86 in which the electronic device 212 is embedded.

In one embodiment, as shown in FIG. 17, instead of using the elastomeric material 230 or uncured or semi-cured elastomeric tube 116, a plurality of sealing elements 152, such as O-rings, are utilized. The form 86 is generally the same as that of FIGS. 15-16. However, disposed around the form 86 are a plurality of generally equally, axially spaced, and radially extending circumferential rings 152, rather than the elastomeric material 230 or uncured or semi-cured elastomeric tube 116 of the previously-described embodiments of the present invention. The assembly is then subjected to a compression molding process to form the medical component 210. Compression molding is carried out for bonding, as needed. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

In another embodiment (not shown), disposed around the form 86 is a thin chemically resistant covering surrounded by the plurality of generally equally, axially spaced, and radially extending circumferential rings 152. The covering may be molded separately and applied to the form 86 or may be directly applied to and molded with the form 86 during molding thereof to enable compatibility with drug product contact. The cover may be formed of any chemically resistant or impervious material, including but not limited to a fluoropolymer (see above examples) or other inert plastic material which lacks the necessary elastomeric qualities for sealing, including but not limited to ethylene tetrafluoroethylene (ETFE), PTFE, perfluoroalkoxy alkanes (PFA), polyvinylidene fluoride (PVDF) and the like. The assembly is then subjected to the above-described compression molding process, wherein the O-rings 152 and cover can be completely cured along with the form 86.

Figure 18A:
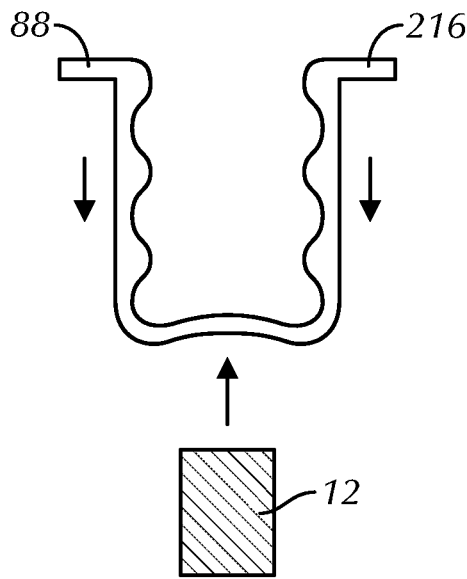
FIGS. 18A-18C illustrate a method of manufacturing a medical component in a one-step molding process according to another preferred embodiment of the present invention.
Figure 18B:
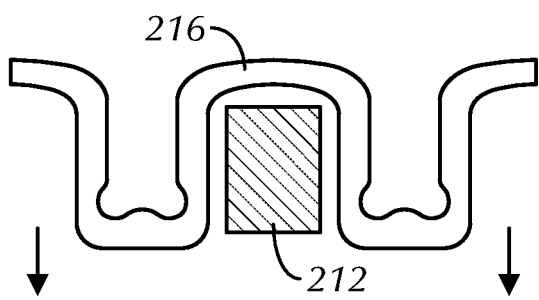
Figure 18C:
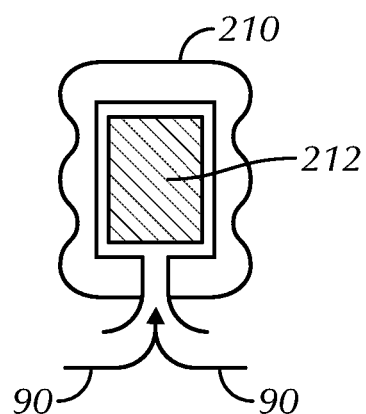

Referring to FIGS. 18A-18C, there is shown another embodiment of a method of manufacturing the medical component 210 in a one-step molding process under predetermined time, heat and pressure conditions. First, an elastomer sheet 216 comprising the elastomeric material is formed. The elastomer sheet 216 may be in a fully cured state, or in a partially or semi-cured state. Next, the elastomer sheet 216 is molded in an inverted shape 88 (i.e., inside out) by any known molding process (e.g., compression molding, injection molding and the like), under predetermined time, heat and pressure conditions. More particularly, the elastomeric material is molded into a shape that is the inverse of the shape of the medical component 10 to be formed. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Next, as shown in FIG. 18B, inversely molded article 88 is contacted with the electronic device 212, and inverted and rolled over the body of the electronic device 212 so as to encapsulate the electronic device 212. The article 88 is then shaped and stretched as necessary to achieve the desired shape and form of the medical component 10. More particularly, the inversely molded article 88 is thermoformed into the shape of the medical component 210. Also, as shown in FIG. 18C, in the end component 210, the trim edges 90 of the elastomer are enclosed, such that the external trim edges that result from conventional molding processes are eliminated. The time, heat and pressure for the thermoforming process will depend upon various factors, such as the specific elastomeric material being used.

Referring to FIGS. 19A-20B, there are shown other embodiments of methods of manufacturing the medical component 210 in a bladder molding process under predetermined time, heat and pressure conditions. The mold 214 is similar to that described above with respect to the process of FIG. 11E.

The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Figure 19A:
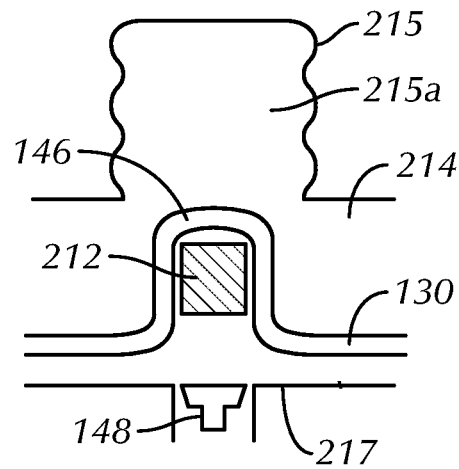
FIGS. 19A-19C schematically illustrate a method of manufacturing a medical component in a one-step molding process according to a further preferred embodiment of the present invention.
Figure 19B:
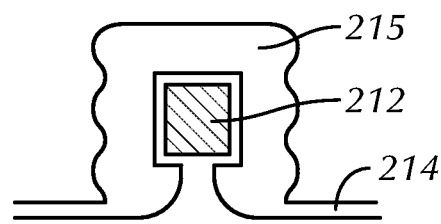
Figure 19C:
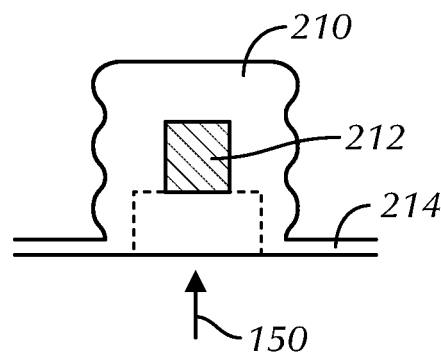

Specifically, referring to FIGS. 19A-19C, in the method of this embodiment, an uncured or partially cured elastomeric sheet 130 includes one or more dimples or recesses 146. Each dimple 146 is configured to receive an electronic device 12. As such, a preform is formed by inserting an electronic devices 212 into each dimple 146 of the uncured or partially cured elastomeric sheet 130. The preform is then arranged in the mold 214. Subsequently, air pressure is applied by an air valve 148 from one side of the mold 214 to force the elastomer sheet 130 and electronic devices 212 into the opposing mold cavity 215a (see FIGS. 19A-19B). The elastomeric material is stretched (e.g., by thermoforming) to the final shape and dimensions of the medical component 210 and then set or cured by the application of heat. Finally, additional elastomeric material 150 may be injected into the mold 214 to fill any voids in the medical component 210 (see FIG. 10C). The later-injected elastomeric material 150 may be the same as or different from the material of the elastomer sheet 130.

Figure 20A:
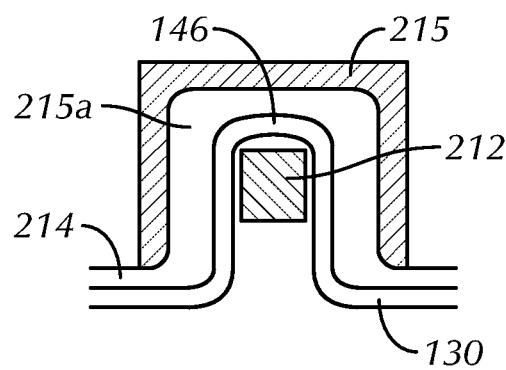
FIGS. 20A-20B schematically illustrate a method of manufacturing a medical component in a one-step molding process according to a further preferred embodiment of the present invention.
Figure 20B:
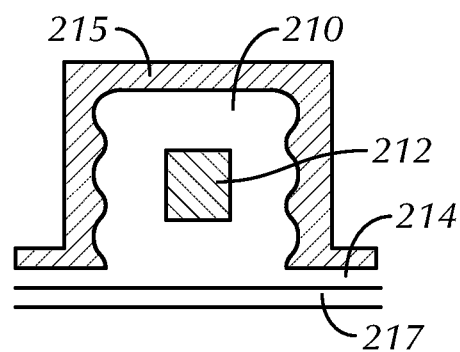

Referring to FIGS. 20A-20B, in an alternative embodiment, external pressure is applied to compress and form the elastomer sheet 130 into the medical component 210. Specifically, the preform of the elastomer sheet 130 with an electronic device 212 arranged in each dimple 146 is positioned in the mold 214, such that each dimple 146 is positioned within one of the cavities (e.g., cavity 215a), as shown in FIG. 20A. Next, the bladder mold 214 is inflated so as to apply external pressure and heat on the elastomer sheet 130 to form the elastomeric material into the shape and dimensions of the medical component 210, as shown in FIG. 20B.

Figure 21A:
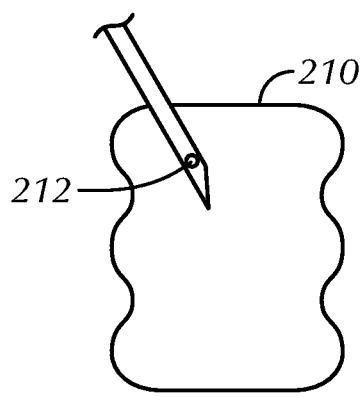
FIGS. 21A-21B schematically illustrate a method of manufacturing a medical component in a one-step molding process according to another preferred embodiment of the present invention.
Figure 21B:
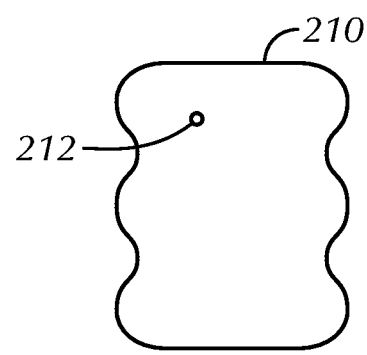
Figure 22A:
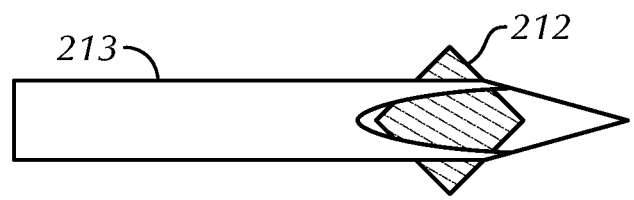
FIGS. 22A-22C illustrate different configurations of a push rod or needle provided with an electronic device for use in the method shown in FIGS. 21A-21B and 23-25.
Figure 22B:
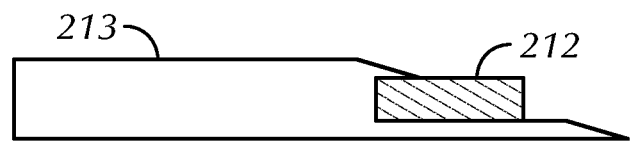
Figure 22C:
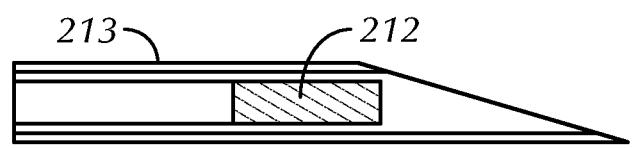

Referring to FIGS. 21A-23, there is shown another embodiment of a method of manufacturing the medical component 210 in a one-step molding process under predetermined time, heat and pressure conditions. Specifically, the medical component 210 is molded in any desired shape, preferably by a conventional one-step compression molding process. However, it will be understood that any known molding process may be utilized (e.g., insert molding, injection molding and the like). In FIGS. 21A-21B, the medical component 210 is shown as a piston or plunger for a cartridge, syringe or vial.

The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Figure 23:
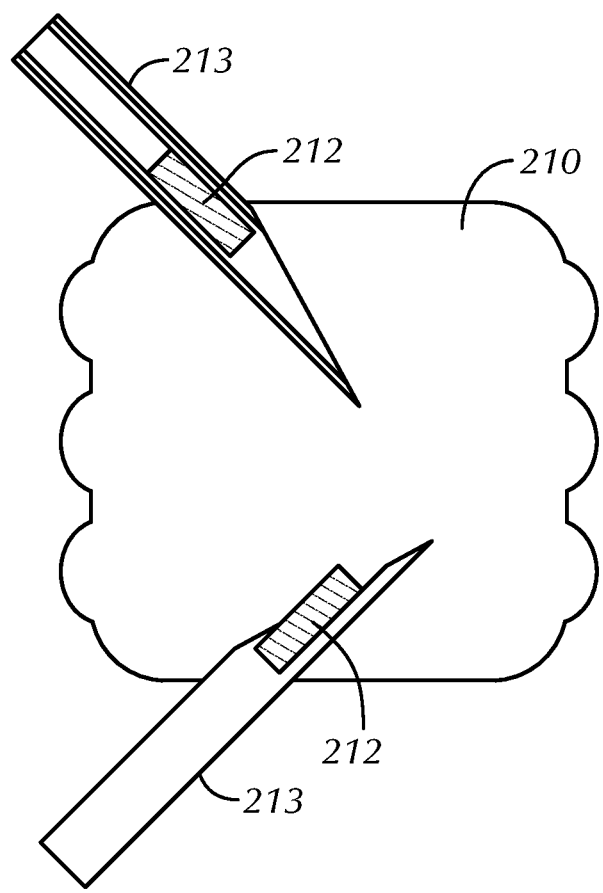
FIG. 23 schematically illustrates a method of embedding an electronic device in a medical component using the push rod or needle shown in FIGS. 22A-22C in accordance with a preferred embodiment of the present invention.

Next, one or more electronic devices 212 may be inserted or injected into the molded medical component 210 by any known technique, such that the one or more electronic devices 212 are embedded in the medical component 210 at the desired location(s). For example, a pushing rod or needle 213 including the electronic device 212 arranged therein (including but not limited to any of the configurations shown in FIGS. 22A-22C) may be used to inject the electronic device 212 into the medical component 210, as shown in FIG. 23. For example, the electronic device(s) 212 may be embedded in the medical component 210 just below a distal surface thereof (e.g., the surface configured to contact the pharmaceutical drug to be delivered to a patient via the medical device for light and/or temperature measurements) or near a lateral surface thereof (e.g., for easy communication with an external sensor). By this method, the location of the electronic device(s) can be easily tailored to any desired location. The electronic device 212 is held in place by the elasticity of the elastomer itself.

Figure 24:
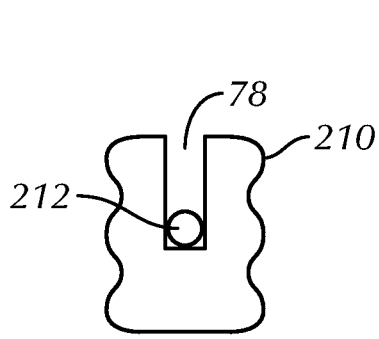
FIG. 24 is a schematic of a method of manufacturing a medical component in a one-step molding process according to another preferred embodiment of the present invention.

Alternatively, as shown in FIG. 24, one or more pilot holes 78 may be formed in the molded medical component 210 and the electronic device 212 is then inserted into the body of the medical component 210 through the pilot hole 78.

Figure 26A:
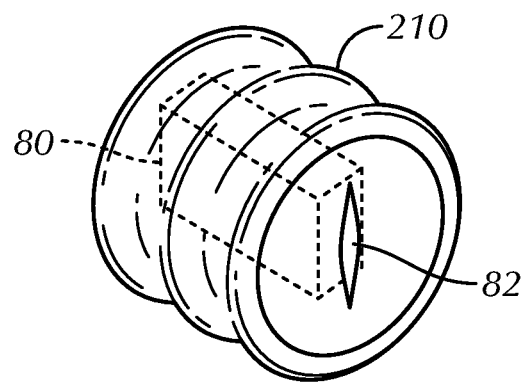
Figure 26B:
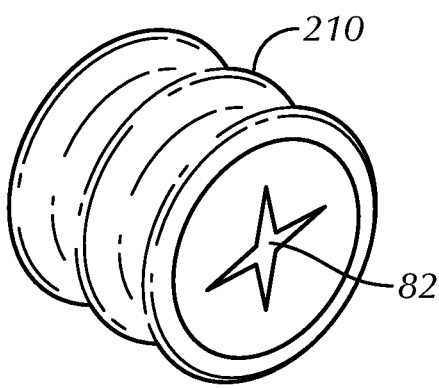
Figure 26C:
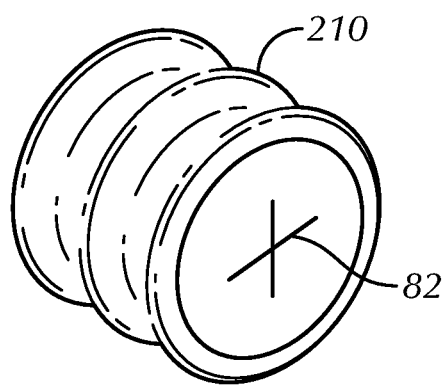
Figure 28C:
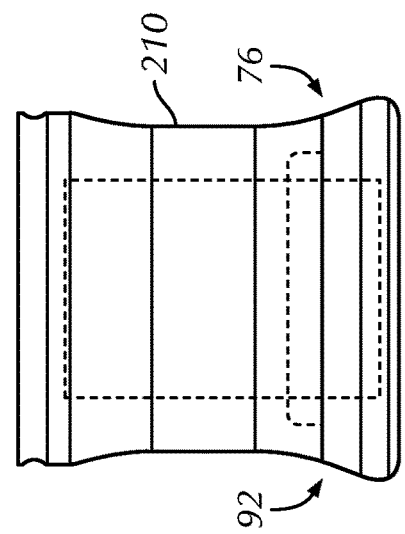
FIGS. 28A-28C illustrate a method of manufacturing a medical component in a two-step molding process according to another preferred embodiment of the present invention.
Figure 28B:
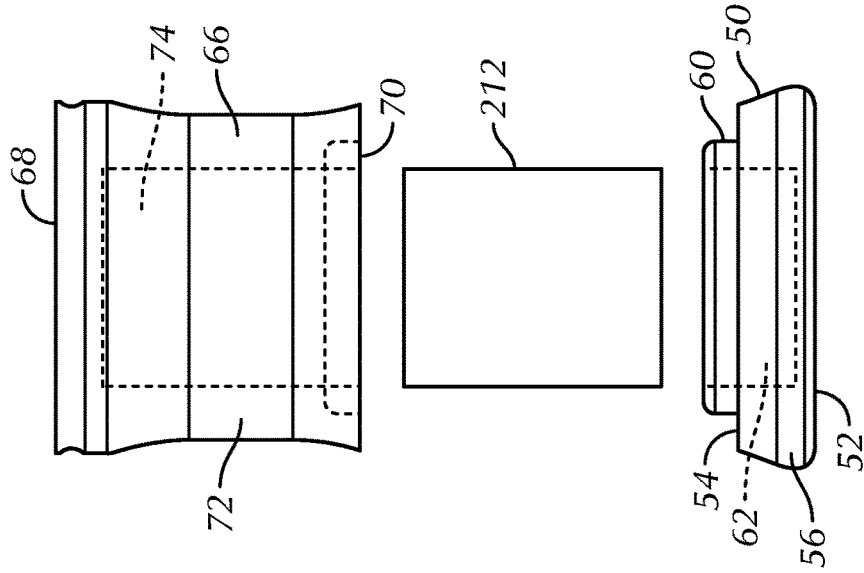
Figure 28A:
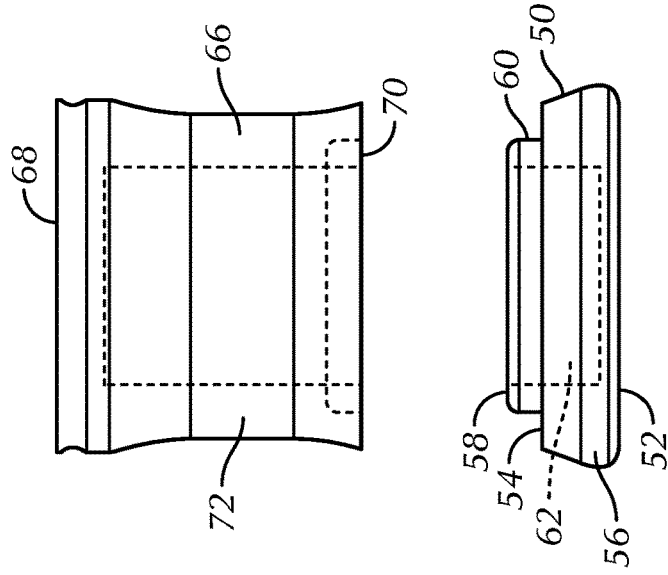

In another embodiment, as shown in FIG. 26A-26C, the medical component 210 may be molded, under the process conditions discussed above, so as to already include one or more cavities 80, each of which is configured to receive one or more electronic devices 212. At the entry of each cavity 80, and particularly in a surface of the molded component, a notch 82 is preferably provided to facilitate insertion of the electronic device 212 into the cavity 80. The notch 82 may have any known form. For example, notch 82 may be a biconvex opening, a Bite Valve™, a plurality of slits, and the like. After the electronic device 212 is inserted into the cavity 80, a piston rod may also be inserted through the same notch 82 and into the cavity 80.

Alternatively, the cavity 80 and notch 82 may be formed while the elastomer is in only a partially cured form, the electronic device 212 is then positioned in the cavity 80 in the partially cured body, and the partially cured body is then compression molded to cure the elastomer to form the medical component 210 and the notch 82 is closed by compression. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Figure 25:
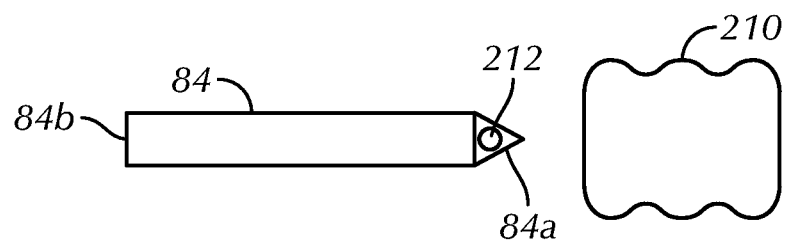
FIG. 25 is a schematic of a method of manufacturing a medical component in a one-step molding process according to another preferred embodiment of the present invention.

In another embodiment, as shown in FIG. 25, after the medical component 210 has been molded, under any of the process conditions discussed above, the electronic device 212 may be inserted or embedded therein via a piston rod 84. More particularly, the piston rod 84 has a first end 84a formed as a spike and an opposing second end 84b. The spiked first end 84a is provided with an electronic device 212 either embedded therein or securely or permanently attached thereto. Beginning with the spiked first end 84a, the piston rod 84 is then inserted into the molded component 210. The molded component 210 may optionally have a cavity 80 and notch 82 as discussed above with reference to FIGS. 26A-26C.

The piercing spike 84a could then remain attached to the actuating rod 84 for power transmission and/or communication with the electronic device 212. The elimination of wireless communications prevents the possibility of interference, allows for greater power transmission with lower losses, and makes tampering/spoofing of signals more difficult. The piercing spike may be made of any known material, such as stainless steel or an injection molded plastic.

Referring to FIGS. 27A-27C, 28A-28C and 30A-30C, there are shown further embodiments of methods of manufacturing the medical component 210 in a two-step molding process. In FIGS. 27A-27C, 28A-28C and 30A-30C, the medical component 210 is depicted as a piston for exemplary purposes, but it will be understood that all of the methods discussed herein could be used to form any medical component.

Referring to FIGS. 27A-27C, the method comprises forming a first member or base member 50 by molding of an elastomeric material (e.g., either a thermoset elastomer or a thermoplastic elastomer). It will be understood that the first member 50 may have any suitable shape which corresponds to the shape of the medical component 210 to be formed. However, as FIGS. 27A-27C relate to a piston 210, the first member 50 has a generally cylindrical shape. Preferably, the first member 50 defines the drug contact end of the piston 210.

The first member 50 preferably has a closed base wall 52, an open top end 54, and a sidewall 56 extending therebetween. The closed base wall 52, open top end 54, and an exterior sidewall 56 define an interior 58 of the first member 50. The interior 58 preferably includes an inner sidewall 60 surrounding a recess 62. The recess 62 is sized and shaped to receive a portion of the electronic device 212 therein.

In order to manufacture the medical component 210 according to the embodiment of FIGS. 27A-27C, the first member 50 is first formed by any known molding method (e.g., compression molding, insert molding, injection molding and the like) in a partially cured state. The process conditions for this molding step are 120 to 310° C. or higher and about 40 to 350 kg/cm$^2$ for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Then, as shown in FIG. 27B, the electronic device 212 is nested within the recess 62 of the first member 50, such that the electronic device 212 rests on or is proximate to the closed base wall 52. It will be understood that any known positioning mechanism or any of the positioning mechanisms described herein may be utilized to secure the electronic device 212 in place within the recess 62. For example, the electronic device 212 and the closed base wall 52 may be provided with corresponding (i.e., mating) protrusions (e.g., a threaded or smooth pin) and recesses or indentations, for purpose of enabling more robust placement and positioning of the electronic device 212.

Finally, in a second molding step, as shown in FIG. 27C, further elastomeric material is overmolded onto the assembled electronic device 212 and first member 50, and cured to form the finished medical component 210 in which the electronic device 212 is fully encapsulated by the elastomeric material. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Preferably, the overmolded elastomeric material is the same as the elastomeric material used to form the first member 50, but it will be understood that a different elastomeric material may be used.

In another embodiment, as shown in FIGS. 28A-28C and 29A-29B, instead of an overmolding process, a second member 66 is formed (e.g., molded under predetermined time, heat and pressure conditions as discussed herein) and assembled with the first member 50 to form the medical component 210. More particularly, the second member 66 is preferably molded from the same elastomeric material used to form the first member 50, but it will be understood that a different elastomeric material may be used. The second member 66 preferably has a closed base wall 68, an opposing open end 70, and a sidewall 72 extending therebetween. The closed base wall 68, open top end 70, and the exterior sidewall 72 define an interior recess 74 of the second member 66. The interior recess 74 is preferably sized and shaped to receive the remaining portion of the electronic device 212 therein. The second member 66 preferably has a complementary shape and size to that of the first member 50 as necessary to achieve the desired shape and size of the medical component 10.

Figure 29A:
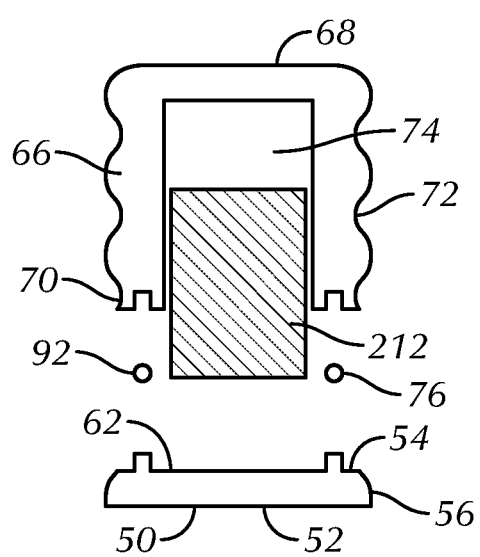
FIGS. 29A-29B are cross-sectional views of a portion of the component manufactured by the method illustrated in FIGS. 28A-28C.
Figure 29B:
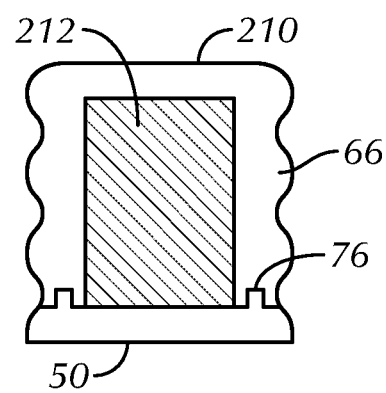
Figure 30A:
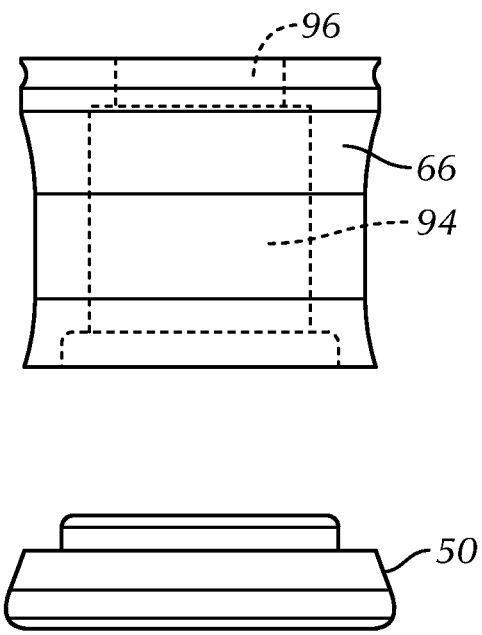
FIGS. 30A-30D illustrate a method of manufacturing a medical component in a two-step molding process according to another preferred embodiment of the present invention.
Figure 30B:
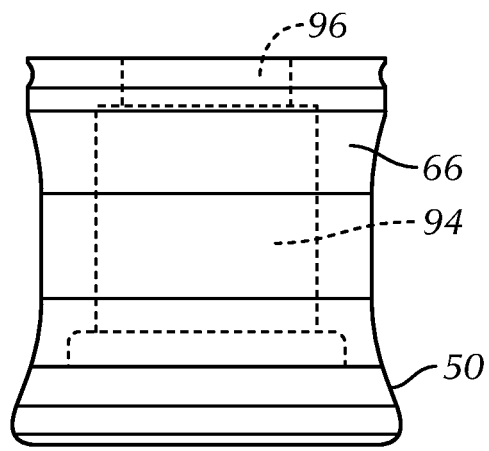
Figure 30C:
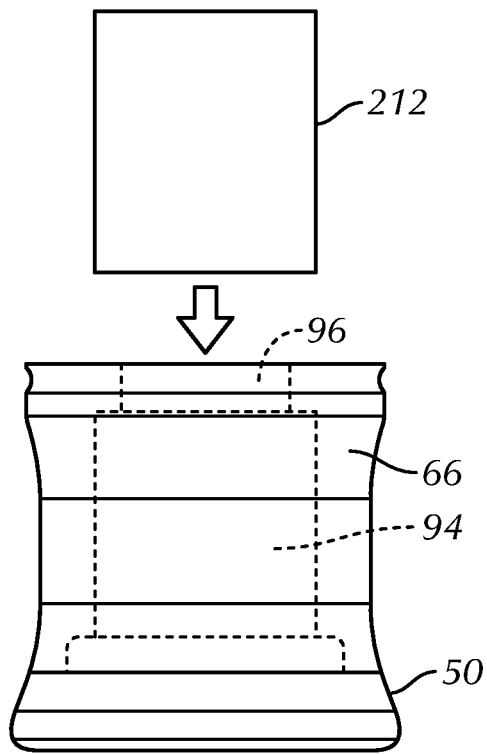
Figure 30D:
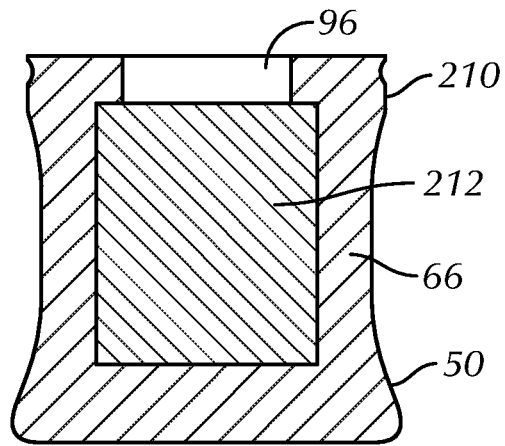
Figure 31A:
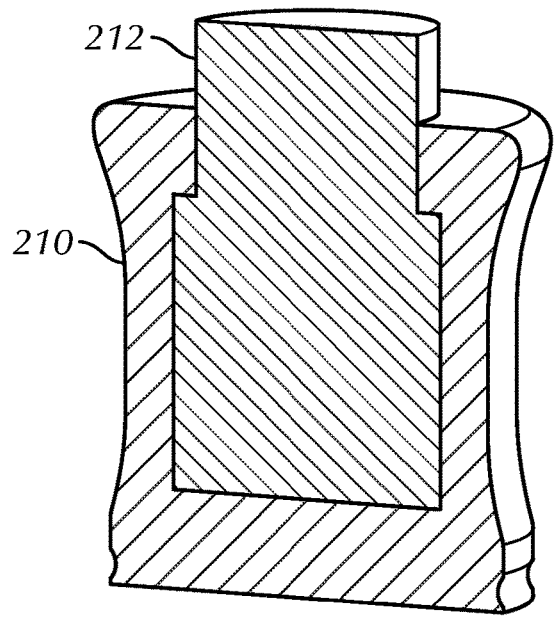
FIGS. 31A-31D show various medical components manufactured by the method shown in FIGS. 30A-30D.
Figure 31B:
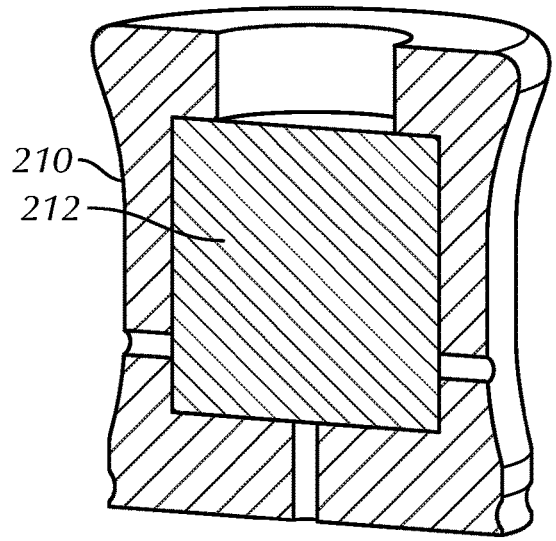
Figure 31C:
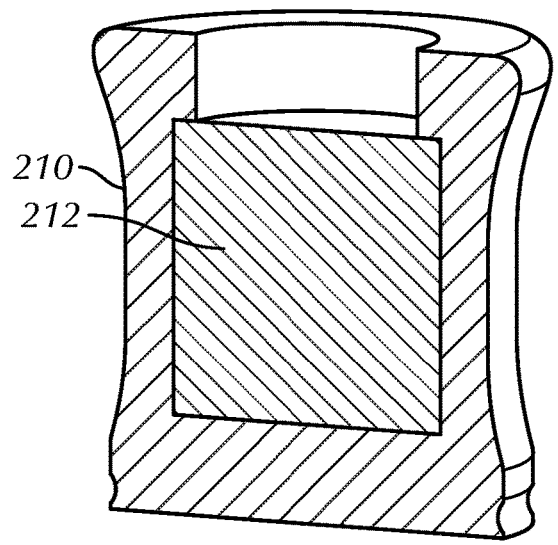
Figure 31D:
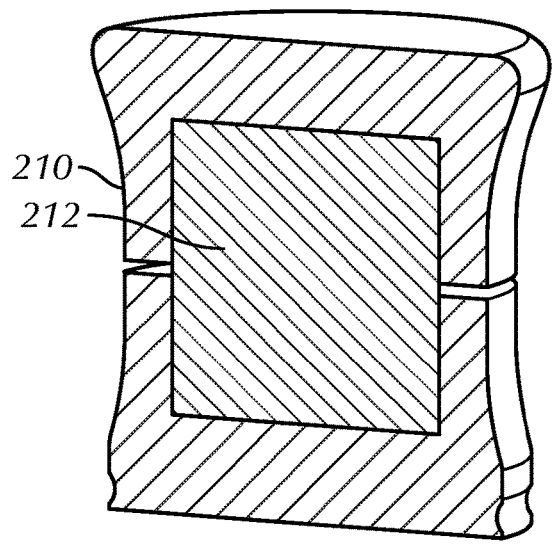

In order to manufacture the medical component 210 according to the embodiment of FIGS. 29A-29B, the first member 50 and second member 66 are first separately formed by any known molding method, under predetermined time, heat and pressure conditions as discussed herein, in partially cured states. The process conditions for these molding steps are 120 to 310° C. and about 40 to 350 kg/cm² for a few seconds to 30 minutes, more preferably about 120 to 70° C. and about 40 to 220 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Then, the electronic device 212 is nested within the recess 62 of the first member 50, such that the electronic device 212 rests on or is proximate to the closed base wall 52. It will be understood that any known positioning mechanism or any of the positioning mechanisms described herein may be utilized to secure the electronic device 212 in place within the recess 62. Next, the second member 66 is assembled with the first member 50 in a mold, such that the open top ends 54, 70 contact each other at an interface 76 and the electronic device 12 is received within the recesses 62, 74 of the first and second members 50, 66.

Next, in accordance with one embodiment, the assembled first and second members 50, 66 are bonded or welded together by heating the entire assembly in the mold to fully cure the elastomeric material under predetermined time, heat and pressure conditions. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Optionally, as shown in FIGS. 29A-29B, a layer of curable gum 92 may be placed at the interface 76 prior to the heating in order to facilitate bonding of the first and second members 50, 66. Such a process, utilizing pre-molded first and second members 50, 66, avoids the possibility of the viscous flow of the elastomer from damaging the electronic device 212 that would occur in, for example, a one-step overmolding process.

Alternatively, in accordance with another embodiment, a localized curing process may be implemented. More particularly, the first and second members 50, 66 may be initially molded in a fully cured state. The process conditions for these molding steps are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Next, the electronic device 212 and first and second members 50, 66 are assembled as discussed above, and bonded or welded together at the interface 76, optionally provided with the gum layer 92, by a directed energy source, such as, but not limited to, ultrasonic welding, microwave heating/curing, and laser heating/curing, that effects localized curing the elastomeric material and gum at the interface 76. The localized curing process protects the encapsulated electronic device 212 from being subjected to extreme conditions. The process conditions for this localized curing step is 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Referring to FIGS. 30A-30D, there is shown another embodiment of a method of manufacturing the medical component 210 in a two-step molding process. First, the first member 50 is molded as described herein with respect to FIGS. 27A-29B. Next, the body of the second member 66 is either overmolded onto the first member 50 (similar to the process of FIGS. 27A-27C) or separately formed and welded to the first member 50 (similarly to the process of FIGS. 28A-29B). The body of the second member 66 preferably includes a pocket or cavity 94 configured to receive the electronic device 212, and an opening 96, for example at a surface opposing to the drug contacting surface of the first body 50 or at a lateral surface, through which the electronic device 212 is inserted in order to be embedded in the cavity 94 within the medical component 210.

FIGS. 31A-31D show various embodiments of the structure and arrangement of the medical component 210 provided with an electronic device 212.

Figure 32A:
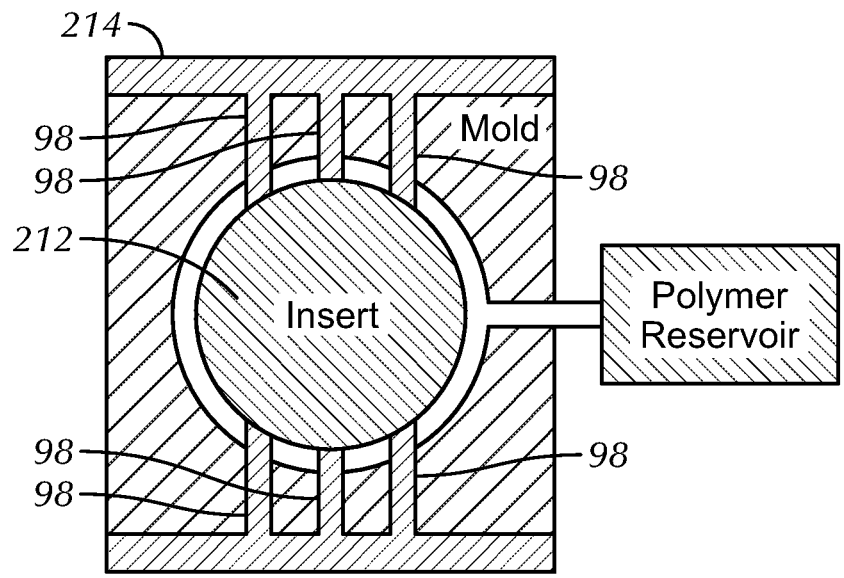
FIGS. 32A-32B illustrate a method of manufacturing a medical component in a one-step molding process according to another preferred embodiment of the present invention.
Figure 32B:
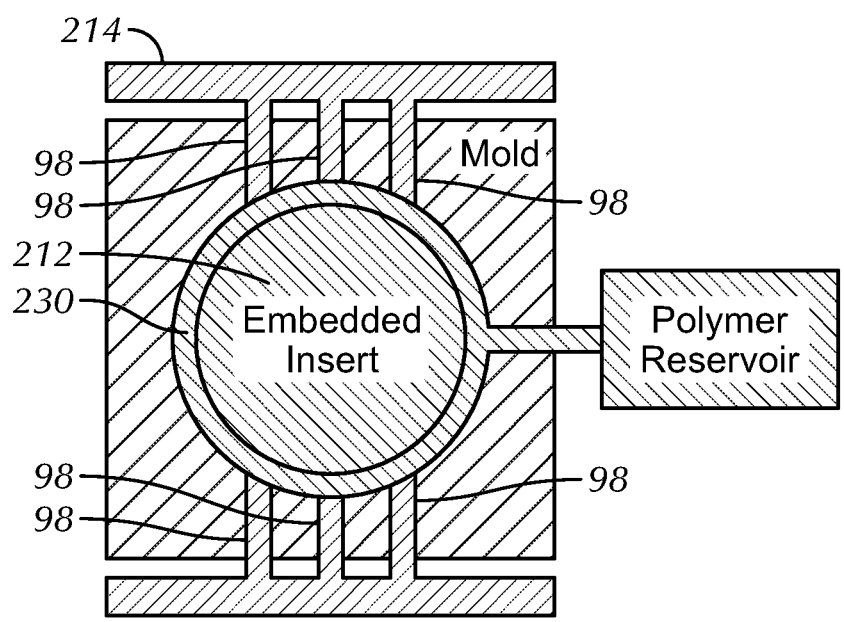

In any of the embodiments disclosed herein, retractable holding pins or protrusions 98 may be used to secure the electronic device 212 in position during the molding process (e.g., compression molding, injection molding and the like, preferably injection molding), as shown in FIGS. 32A-32B. Specifically, a plurality of holding pins 98 are initially used to center the electronic device 212 upon placement in a mold 214. Next, the molding process begins and elastomeric material 230 begins to surround the aligned electronic device 212. When the elastomeric material 230 sufficiently surrounds the aligned electronic device 212 (i.e., to the extent that the electronic device 212 will not be easily dislodged from its center), the holding pins 98 are retracted toward the mold 214 and away from the electronic device 212, thereby allowing the elastomeric material 230 to fully encapsulate the electronic device 212.

A fully encapsulated electronic device 212, as achieved by any of the methods described herein, has the benefit of being fully protected from its environment and would likely be capable of steam sterilization.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An assembly for a container configured to be filled with a pharmaceutical drug, the assembly comprising:
  a piston comprising:
    an electronic device embedded in the piston, the electronic device comprising a power supply;
    a first end comprising a first engagement feature; and
    a second end that opposes the first end, the second end bonded to a protective film, the protective film comprising a first surface that covers an exposed surface of the electronic device, the protective film comprising a second surface that opposes the first surface, and the second surface being configured to contact the pharmaceutical drug when the container is filled; and
  a piston rod comprising a second engagement feature configured to engage the first engagement feature of the piston.

2. The assembly of claim 1, wherein the power supply comprises a battery arranged proximate the second end of the piston and a plurality of wires extending from the first end to the second end of the piston.

3. The assembly of claim 1, wherein the first engagement feature comprises a first thread and the second engagement feature comprises a second thread that corresponds to the first thread, wherein the first thread and the second thread are configured to be interlocked together.

4. The assembly of claim 1, wherein the first engagement feature comprises an annular recess and the second engagement feature comprises an annular protrusion configured to be received in the annular recess.

5. The assembly of claim 1, wherein the first engagement feature comprises a plurality of spaced-apart recesses and the second engagement feature comprises a plurality of spaced-apart protrusions, and each of the plurality of spaced-apart protrusions are configured to be received in a corresponding one of the plurality of spaced-apart recesses.

6. The assembly of claim 1, wherein the piston comprises a first electrical contact and the piston rod comprises a second electrical contact configured to engage the first electrical contact, and wherein an electrical connection is formed when the first engagement feature is engaged with the second engagement feature.

7. The assembly of claim 1, wherein the container comprises a cartridge, a vial, or a syringe.

8. The assembly of claim 1, further comprising a battery, a processor, and a transmitter, wherein the assembly is configured to sense a first signal from the electronic device and at least one of process the first signal from the electronic device as feedback to control an actuator of the container, or send a second signal from the assembly to an external device configured to at least one of monitor the second signal from the assembly or receive the second signal from the assembly and adjust movement of the actuator of the container.

9. The assembly of claim 1, wherein the piston comprises at least one of a thermoset elastomer or a thermoplastic elastomer.

10. The assembly of claim 9, wherein the piston comprises at least one of a butyl elastomer or a halobutyl elastomer.

11. An assembly for a container, the container being configured to be filled with a pharmaceutical drug, the assembly comprising:
  a piston comprising:
    a first end comprising a first engagement feature;
    an electronic device embedded in the piston;
    an electrical contact that is exposed, the electrical contact being connected to the electronic device; and
    a second end bonded to a protective film, the protective film comprising a first surface that covers an exposed surface of the electronic device, the protective film comprising a second surface that opposes the first surface, and the second surface being configured to contact the pharmaceutical drug when the container is filled; and a piston rod comprising:
- a second engagement feature configured to engage the first engagement feature; and
- an electrical contact that is exposed, wherein the electrical contact of the piston rod is configured to engage with the electrical contact of the piston, such that in an assembled position, the electrical contact of the piston is in electrical communication with the electrical contact of the piston rod, and wherein the electronic device comprises at least one of an integrated circuit, a sensor, or a power supply.

12. The assembly of claim 11, further comprising a battery arranged proximate the second end of the piston and a plurality of wires extending from the first end to the second end of the piston.

13. The assembly of claim 11, wherein the first engagement feature comprises a first thread and the second engagement feature comprises a second thread that corresponds to the first thread, wherein the first thread and the second thread are configured to be interlocked together.

14. The assembly of claim 11, wherein the first engagement feature comprises an annular recess and the second engagement feature comprises an annular protrusion configured to be received in the annular recess.

15. The assembly of claim 11, wherein the first engagement feature comprises a plurality of spaced-apart recesses and the second engagement feature comprises a plurality of spaced-apart protrusions, and each of the plurality of spaced-apart protrusions are configured to be received in a corresponding one of the plurality of spaced-apart recesses.

16. The assembly of claim 11, wherein the container comprises a cartridge, a vial, or a syringe.

17. The assembly of claim 11, further comprising a battery, a processor, and a transmitter, wherein the assembly is configured to sense a first signal from the electronic device and at least one of:
- process the first signal from the electronic device as a feedback to control a cartridge, or
- send a second signal from the assembly to an external device that is configured to at least one of monitor the second signal from the assembly or receive the second signal from the assembly, process the second signal from the assembly, and adjust movement of an actuator of the cartridge.

18. The assembly of claim 11, wherein the piston comprises at least one of a thermoset elastomer or a thermoplastic elastomer.

19. The assembly of claim 18, wherein the piston comprises at least one of a butyl elastomer or a halobutyl elastomer.

20. An assembly for a container, the container is configured to be filled with a pharmaceutical drug, the assembly comprising:
a piston comprising:
- an elastomeric material;
- a magnetic material embedded in and fully encapsulated by the elastomeric material;
- a first end comprising a first engagement feature; and
- a second end that opposes the first end, the second end bonded to a protective film, the protective film comprising a first surface that covers an exposed surface of the magnetic material, the protective film comprising a second surface that opposes the first surface, and the second surface being configured to contact the pharmaceutical drug when the container is filled; and a piston rod comprising a second engagement feature configured to engage the first engagement feature of the piston.

21. A system for adjusting a dose of a pharmaceutical drug, the system comprising:
an assembly for a container configured to be filled with the pharmaceutical drug, the assembly comprising:
a piston comprising:
- an electronic device embedded in the piston, the electronic device comprising a sensor;
- a first end comprising a first engagement feature;
- a second end that opposes the first end, the second end bonded to a protective film, the protective film comprising a first surface that covers an exposed surface of the electronic device, the protective film comprising a second surface that opposes the first surface, and the second surface being configured to contact the pharmaceutical drug when the container is filled; and a piston rod comprising a second engagement feature configured to engage the first engagement feature;
a wireless communication unit; and
a controller configured to receive data associated with an administered dose of the pharmaceutical drug and to assess whether the administered dose meets a prescribed parameter.

22. The system of claim 21, wherein the controller is configured to adjust a subsequent dose of the pharmaceutical drug based on whether the administered dose meets the prescribed parameter.

23. A method for adjusting a dose of a pharmaceutical drug, the method comprising:
obtaining a system comprising an assembly for a container, the container configured to be filled with the pharmaceutical drug, the system further comprising a wireless communication unit, and a controller, the assembly comprising:
a piston comprising:
- an electronic device embedded in the piston, the electronic device comprising a sensor;
- a first end comprising a first engagement feature; and
- a second end that opposes the first end, the second end bonded to a protective film, the protective film comprising a first surface that covers an exposed surface of the electronic device, the protective film comprising a second surface that opposes the first surface, and the second surface being configured to contact the pharmaceutical drug when the container is filled; and a piston rod comprising a second engagement feature configured to engage the first engagement feature of the piston;
receiving, by the controller, data associated with an administered dose of the pharmaceutical drug; and
assessing, by the controller, whether the administered dose meets a prescribed parameter.

24. The method of claim 23, further comprising adjusting, by the controller, a subsequent dose of the pharmaceutical drug to be administered based on the assessment of whether the administered dose meets the prescribed parameter.

* * * * *